US009181208B2

(12) United States Patent
Choi et al.

(10) Patent No.: US 9,181,208 B2
(45) Date of Patent: Nov. 10, 2015

(54) 3,6-ANHYDRO-L-GALACTOSE DEHYDROGENASE ACTING ON 3,6-ANHYDRO-L-GALACTOSE, AND PRODUCTION OF 3,6-ANHYDROGALACTONIC ACID BY USING THE ENZYME

(75) Inventors: In-Geol Choi, Seoul (KR); Kyoung Heon Kim, Seoul (KR); Eun Ju Yun, Seoul (KR); Saeyoung Lee, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 13/980,211

(22) PCT Filed: Jan. 25, 2012

(86) PCT No.: PCT/KR2012/000607

§ 371 (c)(1), (2), (4) Date: Jul. 17, 2013

(87) PCT Pub. No.: WO2012/102552

PCT Pub. Date: Aug. 2, 2012

(65) Prior Publication Data

US 2013/0303743 A1 Nov. 14, 2013

(30) Foreign Application Priority Data

Jan. 24, 2011 (KR) ........................ 10-2011-0006631

(51) Int. Cl.

*C12N 15/52* (2006.01)
*C07D 307/20* (2006.01)
*C12N 9/04* (2006.01)
*C12P 17/04* (2006.01)

(52) U.S. Cl.

CPC ............ *C07D 307/20* (2013.01); *C12N 9/0006* (2013.01); *C12P 17/04* (2013.01)

(58) Field of Classification Search

CPC ........................................................ C12N 15/52
USPC ........................................................ 435/190
See application file for complete search history.

(56) References Cited

PUBLICATIONS

Weiner et al. 2008: Complete genome sequence of the complex carbohydrate-degrading marine bacterium, Saccaraphagus degradans Strain 2-40T. PLos Genetics. 4(5): e1000087; 1-13.*

Copeland et al. 2006 (amino acid); Complete sequence of *Pseudoalteromonas altantica* T6c. EMBL CP000388.*

Copeland et al. (2006 (DNA); Complete sequence of *Pseudoalteromonas altantica* T6c. EMBL CP000388.*

Zhong et al. 2001; Sequence analysis of a 101-kilobase plasmid required for agar degradation by a Microscilla isolate. Applied and Environmental Microbiology. 67(12): 5771-5779.*

Mavromatis et al. 2010; Complete genome sequence of Coraliomargarita akajimensis type strain (040KA010-24T). Standards in Genomic Sciences. 2:290-299.*

Hee Taek Kim, et al; "Overexpression and molecular characterization of Aga50D from *Saccharophagus degradans* 2-40; an exo-type β-agarase producing neoagarobiose", Appl. Microbiol. Biotechnol, vol. 86, pp. 227-234, Published online Oct. 3, 2009.

Maria Errea, et al; "Seperation and quantitation of enantiomeric 3,6-anhydrogalactoses by conversion to the corresponding diastereomeric acetylated *sec*-butyl 3,6-anhydrogalactonates", Carbohydrate Research, vol. 311, pp. 235-238, Oct. 1998.

M. Duckworth, et al; "The Structure of Agar Part II. The Use of a Bacterial Agarase to Elucidate Structural Features of The Charges Polysaccharides in Agar", Carbohydrate Research, vol. 16, pp. 435-445, Feb. 1971.

Korea National Statistical Office "Fisheries Production Stattistics" In Korean Language Only, Feb. 23, 2007, 62 pages.

Howard Ochman, et al; "Genetic Applications of an Inverse Polymerase Chain Reaction", Genetics, vol. 120, pp. 621-623, Nov. 1988.

David Shortle, et al; "Directed Mutagenesis with Sodium Bisulfite", Methods in Enzymology, vol. 100, pp. 457-468; Book published by Academic Press, Inc. Copyright ©1983; ISBN 0-12-182000-9.

Mark J. Zoller, et al; "Oligonucleotied-directed mutagenesis using M13-derived vectors: an efficient and general procedure for the production of point mutations in any fragment of DNA", Nucleic Acids Research, vol. 10, No. 20, Oct. 25, 1982, pp. 6487-6500.

M.J. McPherson et al ed.; "PCR: A Practical Approach" PCR Books, IRL Press at Oxford University Press, 1991, soft cover book 9 pages from book.

Eun Ju Yun et al; "Production of 3,6-anhydro-L-galactose from agarose by agarolytic enzymes of *Saccharophagus degradans* 2-40", Process Biochemistry, vol. 46, pp. 88-93, Jan. 2011.

Michael A. Frohman, "Race: Rapid Amplification of cDNA Ends", PCR Protocols: A Guide to Methods and Applications, 11 pages, Copyright ©1990 by Academic Press, Inc.

J. Sambrook; "Protocol 6 Site-specific Mutagenesis by Overlap Extension", Cold Spring Harb Ptotoc, 2006; doi:10.1101/pdb.prot3468; Chapter 4, 11 pages.

* cited by examiner

*Primary Examiner* — Karen Cochrane Carlson
(74) *Attorney, Agent, or Firm* — Ladas & Parry LLP

(57) ABSTRACT

The present invention relates to a novel 3,6-anhydro-L-galactose dehydrogenase and to a novel compound produced therefrom. More specifically, provided is a 3,6-anhydro-L-galactose dehydrogenase which can produce 3,6-anhydrogalactonic acid of a novel type by metabolizing 3,6-anhydro-L-galactose.

7 Claims, 16 Drawing Sheets

FIG. 3 atgaaaattcataacatgaaaaattttatcaacggcgaatatatagcttcacaagctgat > 60
M K I H N M K N F I N G E Y I A S Q A D Ggcgctattgatgtgcttagcccaagcaccggtaaaaaggtaggcgatattccggcagga > 120
G A I D V L S P S T G K K V G D I P A G Tgtgtagaggatgcgcagttggcgctggatacagccaacgcagctcaaaagctgtgggca > 180
C V E D A Q L A L D T A N A A Q K L W A Aaaaaaacgaacagagagcgcgcaaaaatattgcgtgtattcgctgcgaatattcgtgcg > 240
K K T N R E R A K I L R V F A A N I R A Gcggcggatgatttagccaagctgttagtgagcgagcagggtaaattactttctgttgcg > 300
A A D D L A K L L V S E Q G K L L S V A Caaatggaagtagaagccacagcaacgtttatagaatacgcgtgtgataacgcgcttact > 360
Q M E V E A T A T F I E Y A C D N A L T Atagagggcgatattttaccttccgataacccaaacgaaaaaatatatatccacaaagtg > 420
I E G D I L P S D N P N E K I Y I H K V Ccacgcggtgtggttgtggcaattaccgcttggaattttccgttagcactggcgggcaga > 480
P R G V V V A I T A W N F P L A L A G R Aaaataggcccagcacttgttacaggcaatgctatcgtggttaagccaacccaagaaacg > 540
K I G P A L V T G N A I V V K P T Q E T Ccacttgcaacattggcgttaggcgagctagctaatgctgcgggtattcccgccggcgta > 600
P L A T L A L G E L A N A A G I P A G V Ctcaatattgtaaacggccgtggcagtgttgttgggcagcacctgtgcgaaagcccaata > 660
L N I V N G R G S V V G Q H L C E S P I Acccgcttaataaccatgaccggcagcacccctgctgggcagcgtatttaccgcaccagt > 720
T R L I T M T G S T P A G Q R I Y R T S Gccgatcatttaacgccagtaatgctagaactgggcggtaaggcaccatttatcgtaatg > 780
A D H L T P V M L E L G G K A P F I V M Gaagatgccaacttagaaagcgcagtagaggcggcatttactacgcgttatgccaattgc > 840
E D A N L E S A V E A A F T T R Y A N C Ggccaagtgtgtacctgtgccgagcgcctgtatgtacacgaatctatttaccccgctttt > 900
G Q V C T C A E R L Y V H E S I Y P A F Atggataagctacttgagaaggtgaaagcaataaaagtgggcgacccaatggctgccgat > 960
M D K L L E K V K A I K V G D P M A A D Accgatatgggtcccaaggttaatcaaagcgaaatagaaaatattgatgcgctggttaag > 1020
T D M G P K V N Q S E I E N I D A L V K Aagggtattgagcaaggcgcaaccttgctgcatggcggtaagcgcgcgcatgtgcctggc > 1080
K G I E Q G A T L L H G G K R A H V P G Tttgaaggtggcaactggtatgaacccacactgctaggtgatgtgcagcaaagtaatatt > 1140
F E G G N W Y E P T L L G D V Q Q S N I Cttgtgcacgaagaaacgtttgggcctattttacctgtagttaaaattaacagtattgag > 1200
L V H E E T F G P I L P V V K I N S I E Caggctatagagtacaccaacgacagtgagtatggcctttcaacgtatttgtttacgcaa > 1260
Q A I E Y T N D S E Y G L S T Y L F T Q Aaccttaaatatattcatcaatatattgccgaggttgaggccggtgaggtgtatgttaac > 1320
N L K Y I H Q Y I A E V E A G E V Y V N Cgcggtattggtgagcagcaccaaggcttccacaacggttggaagcttagcggggcaggc > 1380
R G I G E Q H Q G F H N G W K L S G A G Ggtgaagatggtcgttacggtttagagcagtacttagagaagaagacagtgtattttgct > 1440
G E D G R Y G L E Q Y L E K K T V Y F A Gaatga > 1446

FIG. 4

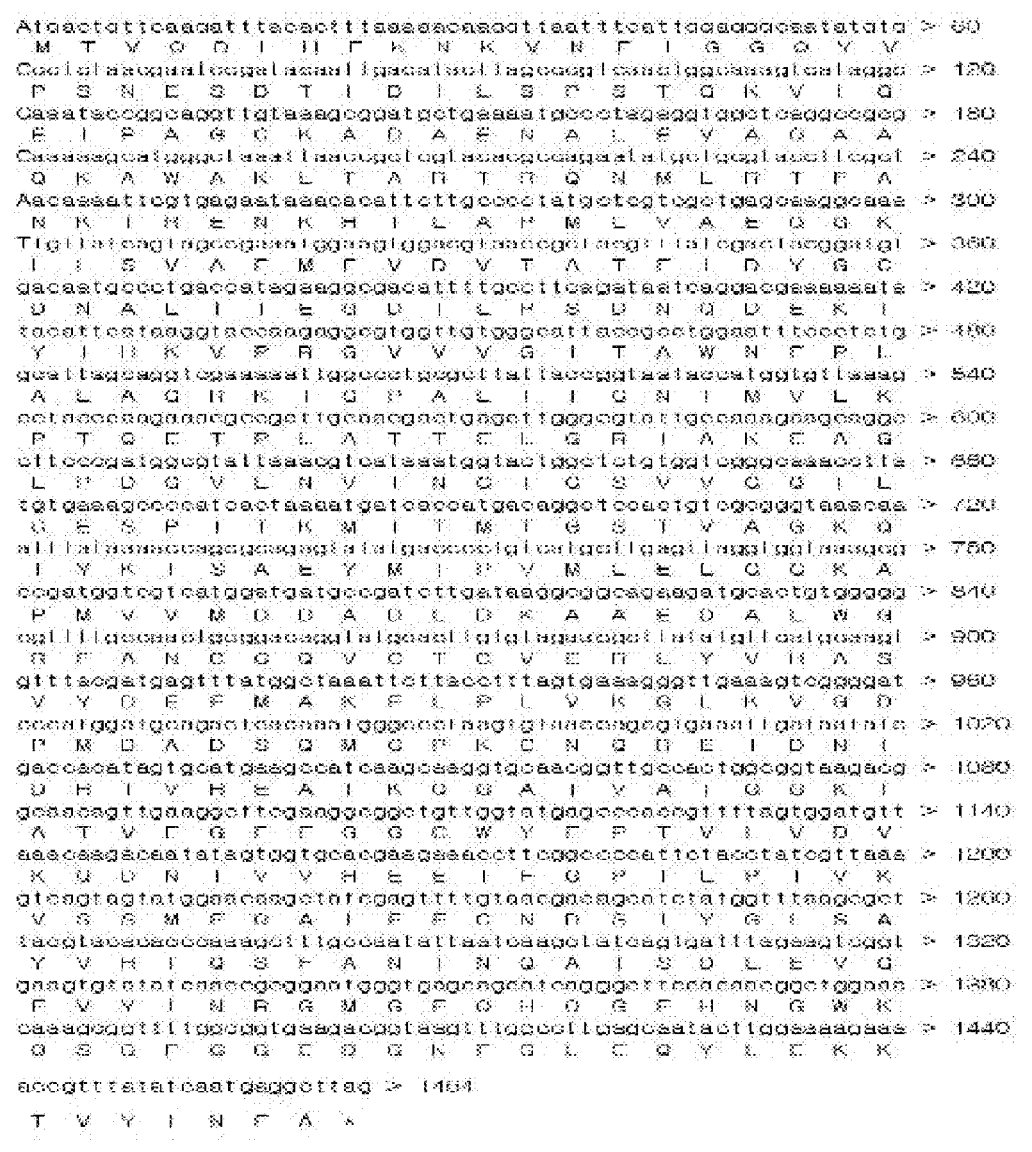

```
Atgactgttcaagatattcactttaaaaacaaggttaatttcattggagggcaatatgtg > 60
 M  T  V  Q  D  I  H  F  K  N  K  V  N  F  I  G  G  Q  Y  V
Ccatctaacgaatcggatacaattgacatactatcattcagtacaggaaaggtcattggc > 120
 P  S  N  E  S  D  T  I  D  I  L  S  F  S  T  G  K  V  I  G
Gaaataccggcaggttgtaaagcggatgctgaaaatgccctagaggtggctcaggccgcg > 180
 E  I  P  A  G  C  K  A  D  A  E  N  A  L  E  V  A  Q  A  A
Caaaaagcatgggctaaattaacagctcgtacacgccagaatatgcttcgtacattcgct > 240
 Q  K  A  W  A  K  L  T  A  R  T  R  Q  N  M  L  R  T  F  A
Aacaaaattcgtgagaataaacacattcttgcccctatgctcgtcgctgagcaaggcaaa > 300
 N  K  I  R  E  N  K  H  I  L  A  P  M  L  V  A  E  Q  G  K
Ttgttatcagtagccgaatggaagtggaggtaaccgctacgttatcgactacggatgt > 360
 I  I  S  V  A  F  M  F  V  D  V  T  A  T  F  I  D  Y  G  C
gacaatgccctgaccatagaaggcgacatttgccttcagataatcaggacgaaaaaata > 420
 D  N  A  L  I  I  E  G  D  I  L  H  S  D  N  Q  D  E  K  I
tacattcataaggtacccagaggcgtggttgtgggcattaccgcctggaatttccctctg > 480
 Y  I  H  K  V  F  R  G  V  V  V  G  I  T  A  W  N  F  P  L
gcattagcaggtcgaaaaattggccctgcgcttattatcggtaatatcatggtgttaaag > 540
 A  L  A  G  R  K  I  G  P  A  L  I  I  G  N  I  M  V  L  K
cctacccaagaaacgccgcttgcaacgactgagcttgggcgtattgccaaagaagcaggc > 600
 P  T  Q  E  T  P  L  A  T  T  E  L  G  R  I  A  K  E  A  G
cttccggatggcgtattaaacgtcattaatggtactggctctgtggttgggcaaacctta > 660
 L  P  D  G  V  L  N  V  I  N  G  L  G  S  V  V  G  Q  I  L
tgtgaaagccccatcactaaaatgatcaccatgacaggctccactgtcggggtaaacaa > 720
 G  E  S  P  I  I  K  M  I  T  M  T  G  S  T  V  A  G  K  Q
atttataaaatcagcgcagaatatatgatcccagtcatgctggagttaggaggtaaagcg > 780
 I  Y  K  I  S  A  E  Y  M  I  P  V  M  L  E  L  G  G  K  A
ccgatggtcgtcatggatgatgccgatcttgataaggcggcagaagatgcactgtggggg > 840
 P  M  V  V  M  D  D  A  D  L  D  K  A  A  E  D  A  L  W  G
cgttttgccaactgcggacaggtatgcacttgtgtagaacgtctatatgttcatgccagt > 900
 R  F  A  N  C  G  Q  V  C  T  C  V  E  R  L  Y  V  H  A  S
gtttacgatgagtttatggctaaattcttacctttagtgaaagggttgaaagtcggggat > 960
 V  Y  D  E  F  M  A  K  F  L  P  L  V  K  G  L  K  V  G  D
ccaatggatgcagactcacaaatgggccctaagtgtaaccagagtgaaattgataatata > 1020
 P  M  D  A  D  S  Q  M  G  P  K  C  N  Q  D  E  I  D  N  I
gaccacatagtgcatgaagccatcaagcaaggtgcaacggttgccactggcggtaagacg > 1080
 D  H  I  V  H  E  A  I  K  Q  G  A  I  V  A  I  G  G  K  I
gcaacagttgaaggcttcgaaggcggctgttggtatgagcccacggtttagtggatgtt > 1140
 A  T  V  E  G  F  F  G  G  G  W  Y  E  P  T  V  I  V  D  V
aaacaagacaatatagtggtgcacgaagaaaccttcggcccaattctacctatcgttaaa > 1200
 K  Q  D  N  I  V  V  H  E  E  I  F  G  P  I  L  P  I  V  K
gtcagtagtatggaacaagctatcgagtttgtcaacgacagcctctatggtttaagcgct > 1260
 V  S  S  M  F  Q  A  I  E  F  C  N  R  S  I  Y  G  L  S  A
tacgtacacacccaaagctttgccaatattaatcaagctatcagtgatttagaagtcggt > 1320
 Y  V  H  I  Q  S  F  A  N  I  N  Q  A  I  S  D  L  E  V  G
gaagtgtatatcaaccgcgggaatgggtgagcagcatcagggctttcacaacggctggaaa > 1380
 E  V  Y  I  N  R  G  M  G  E  Q  H  Q  G  F  H  N  G  W  K
caaagcggttttggcggtgaagacggtaagtttggccttgagcaatacttggaaaagaaa > 1440
 Q  S  G  F  G  G  E  D  G  K  F  G  L  E  Q  Y  L  E  K  K

acggtttatatcaatgaggcttag > 1464

 T  V  Y  I  N  E  A  *
```

FIG. 12
Lineweaver–Burke plot for the product of AHG by SdeAHGD
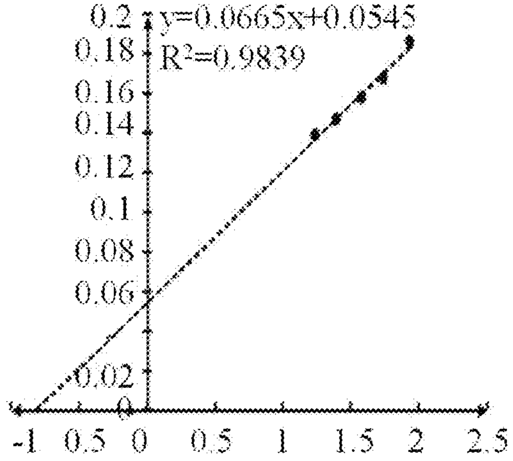
Lineweaver–Burke plot for the product of AHG by PatlAHGD
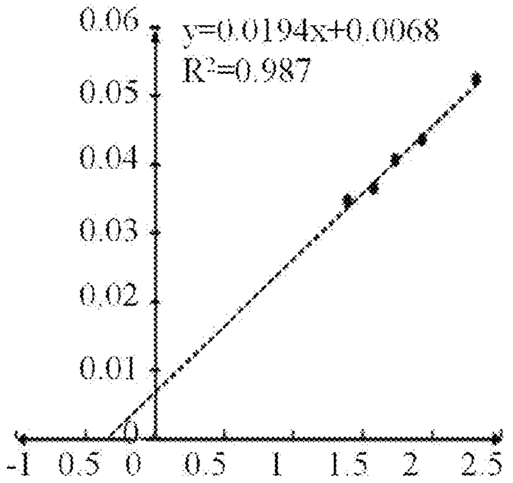

3,6-ANHYDRO-L-GALACTOSE DEHYDROGENASE ACTING ON 3,6-ANHYDRO-L-GALACTOSE, AND PRODUCTION OF 3,6-ANHYDROGALACTONIC ACID BY USING THE ENZYME

CROSS-REFERENCE TO RELATED APPLICATION

This application claims priority to and the benefit of Korean Patent Application No. 2011-0006631, filed Jan. 24, 2011, the disclosure of which is incorporated herein by reference in its entirety.

BACKGROUND

1. Field of the Invention

The present invention relates to 3,6-anhydro-L-galactose dehydrogenase which produces a novel 3,6-anhydrogalatonic acid by metabolizing 3,6-anhydro-L-galactose as a bio energy production technology.

2. Discussion of Related Art

The world is currently facing depletion and rises in prices of petroleum resources, which are a major energy resource, and environmental issues such as global warming derived from an increase of carbon dioxide in the atmosphere by an excessive use of fossil fuels. Therefore, there is an urgent need for the development of a new alternative energy resource which can reduce carbon dioxide emissions. As a major alternative energy, bio-energy in which renewable and abundant plant-based biomass is used as a raw material is being spotlighted. Compared with other alternative energies, bio-ethanol is currently in high demand since it can be used as transportation fuel. Many countries including the United States and Brazil recommend the use of bio-ethanol, which is required by law.

As a first generation biomass currently used for producing bio-ethanol, a sugar-based biomass and a starch-based biomass derived from food resources have a lot of problems in that the use of resources for food causes rising grain prices. In order to overcome such a problem, research on a second generation biomass (ligneous biomass) for energy production is underway. However, a ligneous biomass includes a large amount of lignin, which is a non-biodegradable substance, and therefore ligneous biomass is hardly converted into fermentable monosaccharides. A third generation biomass (marine algae biomass) has advantages in that there is no competition with food resources and it is easily converted into fermentable sugars due to an absence or low content of lignin. Accordingly, the marine algae as a next generation bio-energy source is receiving attention and bio-energy production technologies using the marine algae are being studied actively. In particular, South Korea is surrounded by water on three sides, has rich marine resources, and hence is suitable for using the marine algae as biological resources. Further, South Korea is one of the top ranking global marine algae producing countries along with China, Japan, and North Korea with its annual gross product amounting to 13,754 tons as of 2006. However, there is still room for improvement in terms of utilization thereof (Fisheries Production Statistics, 2006, Agriculture and Fisheries Production Statistics Division, Population and Social Statistics Bureau, National Statistical Office, Korea).

Out of well-known marine algae, research on red algae (for example, *Gelidium amansii*) as a source material is being studied especially actively. More than 70% of the total dry weight of the red algae is polysaccharides capable of being converted into fermentable sugars to be used for microorganisms. A main component of the polysaccharides derived from the red algae biomass is agar with about 60% of total dry weight, and thus agar is considered as a main source for bio-energy production.

Agar is a linear polysaccharide in which 3,6-anhydro-L-galactose (hereinafter referred to as 'L-AHG') and D-galactose (hereinafter referred to as 'D-Gal') are linked together alternately in an α-1,3-glycosidic bond and a β-1,4-glycosidic bond, and is a main component of cell walls in the red algae. Agar includes agaropectin and agarose. Agaropectin has a same basic structure as agarose but differs from agarose in that it has substituent groups such as a sulfate group, pyruvic acid, and glucuronic acid (*Carbohydrate Research* (1971) 16:435-445).

Up to now, different types of microorganisms which can decompose agar have been identified. Among them, *Saccharophagus degradans* 2-40 (hereinafter referred to as '*S. degradans*'), which was first isolated in Chesapeake Bay in Virginia, USA, is a rod-shaped, aerobic marine microorganism, and a complete genome sequence thereof has been reported. *S. degradans* can decompose at least 10 or more complex polysaccharides, including agar, and has an agar catabolic system which allows agar to be used in metabolic processes. Enzymes used in the agar catabolic system are divided into four groups: GH16, GH50, GH86, and GH117. The groups other than GH117 are estimated as β-agarase, and an Aga50D enzyme belonging to the GH50 group has been reported to produce neoagarobiose (hereinafter referred to as 'NA2'), which is a disaccharide, as a final product (*Appl Micro boil Biotechnol* 86:227-234, 2010). Moreover, reports have revealed that neoagarobiose hydrolysis enzyme (hereinafter referred to as 'NABH') belonging to the GH117 group cuts an α-1,3-bond of NA2 (disaccharide). Microorganisms that metabolize agar can convert agar into a fermentable sugar, D-Gal, and a non-fermentable sugar, L-AHG, using agarase. In order to produce bio-energy using the marine algae, pre-treatments are essential so as to convert the marine algae into fermentable sugars. However, L-AHG (monosaccharide) produced in the metabolic process is not used as a fermentable sugar in general microorganisms, thereby decreasing production yield of bio-energy. Furthermore, a metabolic pathway of D-Gal in many types of microorganisms is well known but research on L-AHG metabolic processes in the microorganisms which use agar as a carbon source has not been reported. As a result, in order to produce bio-energy using L-AHG, research on L-AHG metabolic process of the microorganisms which use agar as a carbon source is required to know an accurate metabolic pathway.

SUMMARY OF THE INVENTION

It is an object of the present invention to provide a novel enzyme which metabolizes 3,6-anhydro-L-galactose.

It is another object of the present invention to provide a novel compound produced by the novel enzyme.

In order to achieve the above-described purposes, the invention provides 3,6-anhydro-L-galactose dehydrogenase having amino acid sequence as set forth in SEQ ID NOs: 1 to 4.

The invention further provides a gene encoding 3,6-anhydro-L-galactose dehydrogenase.

The invention still further provides a recombinant vector containing the gene encoding 3,6-anhydro-L-galactose dehydrogenase.

The invention still further provides a transformant which is transformed with the recombinant vector.

The invention still further provides a method of producing 3,6-anhydro-L-galactose dehydrogenase which includes a step of obtaining 3,6-anhydro-L-galactose dehydrogenase from a culture of the transformant.

The invention still further provides a method of producing a compound of the chemical formula 1 which includes a step of reacting 3,6-anhydro-L-galactose dehydrogenase with 3,6-anhydro-L-galactose using nicotinamide adenine dinucleotide phosphate (hereinafter, referred to as 'NADP') as a cofactor.

[Chemical formula 1]

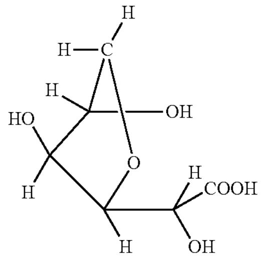

The invention still further provides a compound of the chemical formula 1.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 3 illustrates sdeAHGD gene sequences and amino acid sequences derived from *S. degradans* 2-40.

FIG. 4 illustrates patlAHGD gene sequences and amino acid sequences derived from *Pseudoalteromonas atlantica* (hereinafter referred to as '*P. atlantica*').

FIG. 12 illustrates a reaction kinetic analysis of SdeAHGD and PatlAHGD of the invention.

DETAILED DESCRIPTION OF EXEMPLARY EMBODIMENTS

Figure 1:
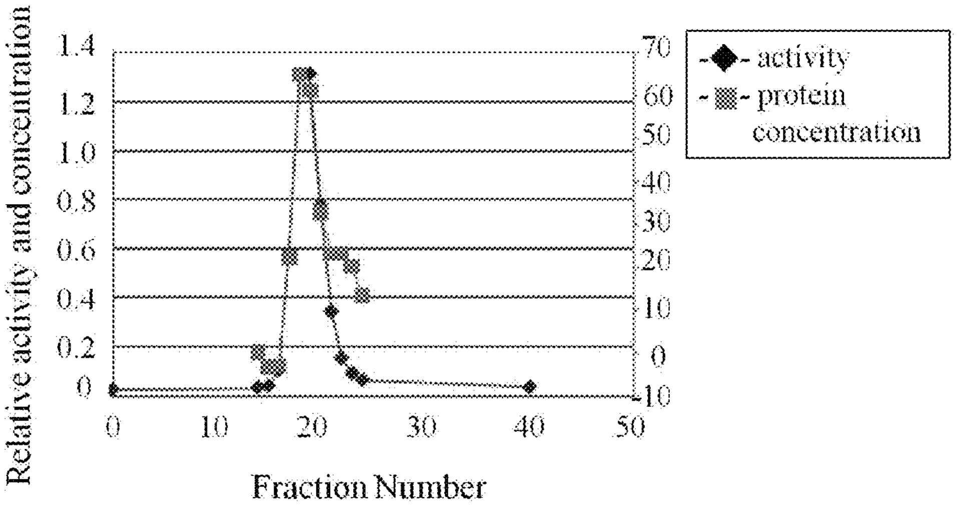
FIG. 1 illustrates a reaction comparison of an active fraction protein using L-AHG as a substrate and activities based on the fractions.

Hereinafter, the present invention will be described in detail with respect to Examples according to the present invention and Comparative Examples not according to the present invention, but the scope of the present invention is not limited thereto.

The inventors of the present invention tried to identify an enzyme protein in which 3,6-anhydro-L-galactose (referred to as 'L-AHG') is used as a substrate in *S. degradans* 2-40 or *P. atlantica* using agarose as a carbon source. The identified enzyme has been confirmed as L-AHG dehydrogenase (hereinafter referred to as 'AHGD') in which an aldehyde group on carbon No. 1(C1) of L-AHG is oxidized to a carboxyl group so as to make 3,6-anhydrogalatonic acid (a compound represented by following chemical formula 1) with the help of an NADP cofactor.

Therefore, the present invention provides 3,6-anhydro-L-galactose dehydrogenase having amino acid sequences as set forth in SEQ ID NOs: 1 to 4.

3,6-anhydro-L-galactose dehydrogenase may have amino acid sequences as set forth in SEQ ID NOs: 1 to 4, and may include amino acid sequences having a homology of 80% or more, 85% or more, specifically 90% or more, and more specifically 95% or more (for example, 98% or more) with respect to the corresponding amino acid sequences. The homology search of the protein may be performed with an amino acid sequence database (for example, SWISS-PROT and PIR), a DNA sequence database (for example, DDBJ, EMBL and GenBank), or an amino acid sequence database deduced from DNA sequences using a program such as BLAST and FASTA through the Internet.

In addition, the enzyme of the invention may include all mutants having a desired activity of the invention generated by mutations such as one or more of substitutions, deletions, inversions, and translocations in the amino acid sequences. The amino acid substitution is called ‘conservative substitution.’ For example, Ala, Val, Leu, Ile, Pro, Met, Phe and Trp are classified as a non-polar amino acid group and have similar properties. Non-charged amino acids include Gly, Ser, Thr, Cys, Tyr, Asn and Gln. Acidic amino acids include Asp and Glu. Basic amino acids include Lys, Arg and His. The mutants may be generated by employing, for example, site-directed mutagenesis (*Nucleic Acid Res.,* 10, 6487 (1982); *Method in Enzymol.,* 100, 448 (1983); ‘Molecular Cloning 2nd Edition,’ Cold Spring Harbor Laboratory Press (1989); and ‘PCR A Practical Approach,’ IRL Press, 200 (1991)).

The enzyme may be derived from *S. degradans* 2-40 or *P. atlantica*, but is not limited thereto, and may include all transformants expressing the enzyme.

3,6-anhydro-L-galactose dehydrogenase can be prepared by peptide synthesizing methods known in the art, for example, by synthesizing in vitro with a gene recombination, a protein expression system, or a peptide synthesizer.

3,6-anhydro-L-galactose dehydrogenase may exhibit an excellent enzyme activity under the conditions of pH 7 to 11 at 20 to 90° C., and more specifically pH 9 to 10 at 25 to 40° C.

The invention further relates to a gene encoding 3,6-anhydro-L-galactose dehydrogenase.

The gene of the invention has a physico-chemical activity of 3,6-anhydro-L-galactose dehydrogenase, and includes a polynucleotide encoding a protein which includes amino acid sequences as set forth in SEQ ID NOs: 1 to 4 in which one or more amino acids are deleted, substituted, inserted, and/or added.

Those skilled in the art may appropriately obtain a homolog of the polynucleotide of the invention by deletions, substitutions, insertions, and/or additions with the polynucleotide of SEQ ID NO: 5 by employing, for example, the site-directed mutagenesis (*Nucleic Acid Res.,* 10, 6487 (1982); Methods in Enzymol., 100, 448 (1983); ‘Molecular Cloning 2nd Edition,’ Cold Spring Harbor Laboratory Press (1989); and ‘PCRA Practical Approach,’ IRL Press, 200 (1991)).

The polynucleotide homolog of the invention includes a nucleotide as set forth in SEQ ID NOs: 5 to 8 and a polynucleotide that hybridizes the polynucleotide encoding a protein having physico-chemical properties of the invention under stringent conditions. The phrase ‘the polynucleotide that hybridizes under stringent conditions’ refers to a polynucleotide that hybridizes one or more of probe DNAs having at least 20 consecutive amino acid residues, preferably at least 30 consecutive amino acid residues of the amino acid sequence (for example, 40, 60, or 100 consecutive amino acid residues) arbitrarily selected from one sequence among SEQ ID NOs: 5 to 8 with ECL direct nucleic acid labeling and detection systems (Amersham Pharmacia Biotech) under the conditions described in the manual, for example, washing with the primary wash buffer solution comprising 0.5×SSC at 42° C.

The polynucleotide of the invention includes an isolated polynucleotide. The term ‘isolated nucleotide’ refers to a polynucleotide that has different forms, compared to the naturally occurring polynucleotide forms. For example, the isolated polynucleotide includes a polynucleotide and a vector integrated into the genome of another organism. Moreover, the isolated polynucleotide includes a polynucleotide obtained as cDNA, a PCR product, or a restriction fragment, and further includes a polynucleotide used as a part of polynucleotide encoding a fusion protein.

The polynucleotide encoding 3,6-anhydro-L-galactose dehydrogenase of the invention may be isolated by methods given below: designing PCR primers based on a nucleotide sequence in SEQ ID NO: 5, and performing a PCR using a cDNA library or chromosomal DNA derived from reductase-producing strains as a template so as to obtain DNA of the invention.

The polynucleotide of the invention may be prepared using a DNA fragment obtained as a probe such that a chromosomal DNA restrict enzyme fragment derived from 3,6-anhydro-L-galactose dehydrogenase producing strains is introduced into a phage or a plasmid by, for example, colony hybridization and plaque hybridization and screening is performed on the library (a) obtained by transformation of *E. coli* cells with the phage or the vector, or the cDNA library (b).

Alternatively, the polynucleotide of the invention may be obtained by: analyzing the nucleotide sequence of a DNA fragment obtained by PCR; designing PCR primers based on the analyzed sequence for extending a strand to the outside of the known DNA sequence; digesting the chromosomal DNA of reductase-producing strains with an appropriate restriction enzyme; and then performing reverse-PCR by a self-cyclizing reaction using the DNA as a template (Genetics, 120, 621-623 (1988)). Furthermore, the polynucleotide of the invention may be obtained by the RACE method (Rapid Amplification of cDNA End, ‘PCR Jikken Manual (Manual for PCR experiments),’ 25-33, HBJ Publishing Bureau).

In addition to the genomic DNA and cDNA cloned by the methods described above, the polynucleotide of the invention may include synthesized DNA.

The invention relates a recombinant vector containing the gene encoding 3,6-anhydro-L-galactose dehydrogenase.

The term ‘recombinant vector’ of the invention is a vector capable of expressing a target protein in a suitable host cell and refers to a genetic construct that includes essential regulatory elements to which a gene insert is operably linked so as to be expressed in the host cell.

The vector includes a plasmid vector, a cosmid vector, a bacteriophage vector, a viral vector or the like, but is not limited thereto. The suitable expression vector includes a promoter, an operator, an initiation codon, a termination codon, and expression regulatory elements such as a polyadenylation signal and an enhancer in addition to signal sequences for membrane targeting or secretion, or a leader sequence, and may be prepared in various ways depending on the purpose. The promoter of the vector may be constitutive or inducible. Furthermore, the expression vector includes a selection marker for selecting a host cell containing the vector and a replicable expression vector includes a replication origin.

The recombinant vector of the invention may be prepared by inserting a nucleic acid encoding 3,6-anhydro-L-galactose dehydrogenase into an expression vector for common *E. coli* strains and pBT21a (hereinafter referred to as ‘pB2’). In an embodiment of the invention, the pB2 was used as an *E. coli* expression vector, but the invention is not limited thereto, and all of the commonly available *E. coli* expression vectors can be used without restriction.

In the embodiment of the invention, a recombinant vector, for example, pB2 vector+sdeAHGD or pB2 vector+patlAHGD (cleavage map in FIG. 6) may be prepared by inserting a DNA fragment containing 3,6-anhydro-L-galactose dehydrogenase encoding gene (SEQ ID NOs: 5 to 8) of the invention with the pB2 vector serving as an *E. coli* expression vector.

The invention relates to a transformant which is transformed with the recombinant vector.

The transformation includes any methods in which nucleic acid is introduced into organisms, cells, tissues, or organs, and may be performed with a suitable standard technology depending on the host cell, as is known in the art. Such transformation methods include electroporation, protoplast fusion, calcium phosphate ($CaPO_4$) precipitation, calcium chloride ($CaCl_2$) precipitation, agitation with silicon carbide fiber, *agrobacterium*-mediated transformation, PEG, dextran sulfate, lipofectamine or the like, but are not limited thereto.

Moreover, since formulas and expression amounts of the protein differ depending on the host cell, the most suitable host cell for the purpose may be selected.

The host cell includes prokaryotic host cells, for example, *Escherichia coli, Bacillus subtilis, Streptomyces, Pseudomonas, Proteus mirabilis*, or *Staphylococcus*, but is not limited thereto. Further, the host cell includes lower eukaryotes such as fungi (for example, *Aspergillus*) and yeasts (for example, *Pichia pastoris, Saccharomyces cerevisiae, Schizosaccharomyces, Neurospora crassa*), or cells derived from higher eukaryotes such as insect cells, plant cells, and mammalian cells.

The transformant may be easily prepared by introducing the recombinant vector into an arbitrary host cell. According to the embodiment of the invention, the transformant may be prepared by introducing the recombinant vector pB2 vector+sdeAHGD or pB2 vector+patlAHGD (cleavage map in FIG. 6) expressing 3,6-anhydro-L-galactose dehydrogenase into *E. coli* strains BL21(DE3).

The invention relates to a method of producing 3,6-anhydro-L-galactose dehydrogenase which includes a step of obtaining 3,6-anhydro-L-galactose dehydrogenase from a culture of the transformant.

3,6-anhydro-L-galactose dehydrogenase is preferably purified by culturing the transformant according to normal culture methods. In 3,6-anhydro-L-galactose dehydrogenase, a part of amino acid sequences may be transformed as long as metabolic capability of the insert introduced into the recombinant vector, that is, 3,6-anhydro-L-galactose, is not affected according to the encoding gene sequence. The transformation refers to a transformation by deletions, insertions or substitutions.

A method of producing the enzyme according to the embodiment of the invention is given below. First, the transformant expressing 3,6-anhydro-L-galactose dehydrogenase is cultured, and then the culture is collected to prepare a cell-free extract by cell lysis in the buffer solution containing reducing agents (for example, 2-mercaptoethanol) and protease inhibitors (for example, phenylmethanesulfonyl fluoride).

A desired enzyme may be purified from the cell-free extract according to fraction methods based on protein solubility (precipitation with organic solvents and salting out with ammonium sulfate), cation exchange chromatography, anion exchange chromatography, gel filtration, hydrophobic chromatography, and an appropriate combination of affinity chromatographs using, for example, complexing agents, dyes, and antibodies. For example, the enzyme of the invention may be purified as one band in electrophoresis by a series of processes using hydrophobic chromatography with phenyl sepharose, anion exchange chromatography with a Mono Q, hydrophobic chromatography with butyl sepharose, and absorption chromatography with hydroxyapatite.

According to the embodiment of the invention, the enzyme having a size of about 52 kDa is obtained as an analysis result of 10% of SDS-PAGE.

The invention relates a polyclonal antibody that specifically binds to 3,6-anhydro-L-galactose dehydrogenase.

A method of producing the polyclonal antibody is not particularly limited, but preferable follows methods given below.

3,6-anhydro-L-galactose dehydrogenase of the invention is injected into specific pathogen free (SPF) animals one or several times for immunization. After a predetermined time from the final immunization, the polyclonal antibody with respect to 3,6-anhydro-L-galactose dehydrogenase of the invention is obtained by extracting serum from the whole blood.

As long as animals commonly used for immunization are used, the immunization animals are not limited particularly, but rats are preferable. The number of injections, periods, and injection methods for immunization are changed or modified by those skilled in the art and hence not particularly limited.

The invention relates a method of producing a compound of the chemical formula 1 which includes a step of reacting 3,6-anhydro-L-galactose dehydrogenase with 3,6-anhydro-L-galactose using NADP as a cofactor.

[Chemical formula 1]

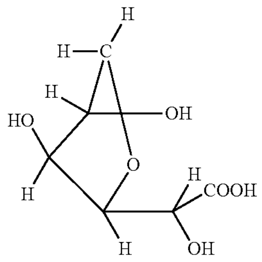

The invention provides a compound of the chemical formula 1.

Since 3,6-anhydro-L-galactose dehydrogenase can oxidize 3,6-anhydro-L-galactose (hereinafter referred to as 'L-AHG'), when reacting with NADP as a cofactor, an aldehyde group on carbon No. 1 of L-AHG is oxidized to a carboxyl group so as to make a compound of the chemical formula 1, that is, 3,6-anhydrogalactonic acid.

3,6-anhydro-L-galactose dehydrogenase may have any one of amino acid sequences as set forth in SEQ ID NOs: 1 to 4, and moreover, can be encoded from any one of sequences as set forth in SEQ ID NOs: 5 to 8.

The enzyme may be derived from, for example, *S. degradans* 2-40, *P. adantica, Microscilla* sp. PRE1 or *Coraliomargarita akajimensis*, but is not limited thereto, and may include all transformants expressing the enzyme.

The reaction may be performed under the conditions of pH 7 to 11 at 20 to 90° C. and more specifically pH 9 to 10 at 25 to 40° C., but is not limited thereto.

The invention provides 3,6-anhydro-L-galactose dehydrogenase which is a novel enzyme isolated from marine algae capable of producing a novel 3,6-anhydrogalatonic acid by oxidizing 3,6-anhydro-L-galactose.

With 3,6-anhydro-L-galactose metabolizing process using the enzyme, it is expected to increase production yield of bio-energy derived from the marine algae.

Example 1

Figure 2:
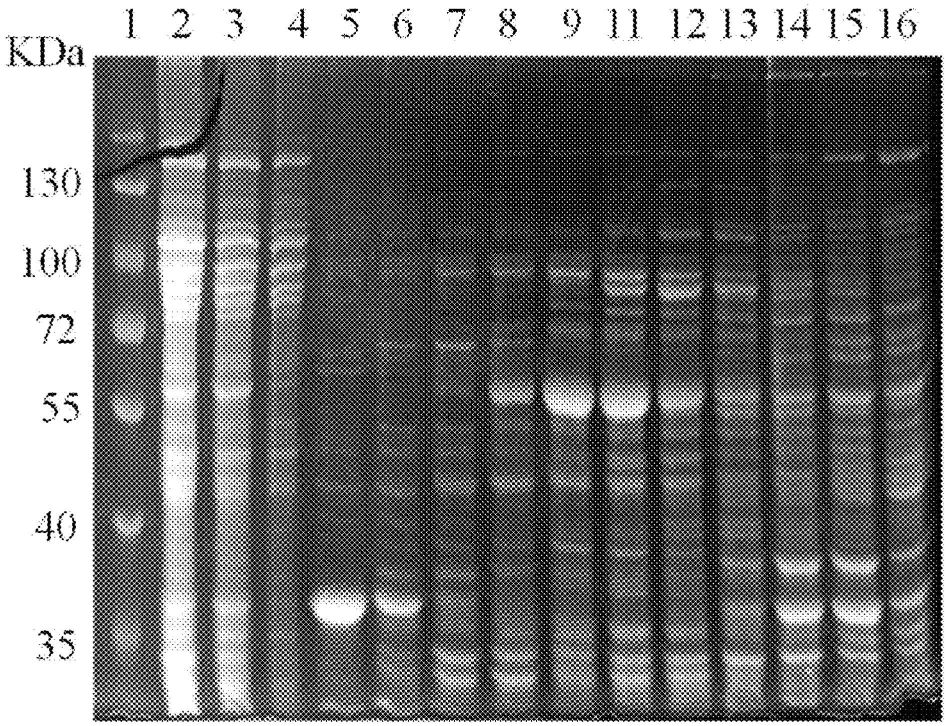
FIG. 2 illustrates an analysis result of 10% of SDS-PAGE of the active fraction enzyme, in which lane 1 indicates a molecular size marker, lane 2 indicates a crude extract, lane 3 indicates a loading sample, lane 4 indicates a sample washed with 10 mM of imidazole, and lanes 5 to 16 indicate fraction numbers 14 to 25.

Preparing an Active Fraction of Enzyme Having L-AHG as a Substrate from *S. Degradans* 2-40° C. rude Extract A single colony of *S. degradans* 2-40 (hereinafter referred to as 'sde') was cultured in 10 mL of a minimal medium (2.3% sea salt, 0.1% yeast extract, and 0.05% $NH_4Cl$ aqueous solution) containing 0.2% agar for 24 hours at 30° C., and then the 10 mL of cultured strain was input into 1 L of a minimal medium with same composition as the above and was further cultured for 24 hours at 30° C. The cultured biomass was recovered by centrifuging for 30 min at 4000 rpm and was sonicated with a Sonifier 450 (Branson, USA) to make crude extract. The crude extract was centrifuged for 1 hour at 15000 rpm and 4° C. and then separated into supernatant (crude enzyme extract) and sediment (cell fragment). The supernatant was fractioned with anion exchange chromatography using a HiTrap Q column (GE Healthcare, USA). Finally, using a desalting column (GE Healthcare, USA) with the obtained fraction, a buffer solution (20 mM of Tris-HCl and pH 8.0) was prepared. A composition and size of the protein in each fraction were confirmed with 10% of SDS-PAGE method, and active fractions were obtained by activity verification of the enzyme having L-AHG as a substrate, as described below (FIGS. 1 and 2).

Experimental Example 1

Measuring an Activity of the Enzyme Having L-AHG Included in the Fraction as a Substrate The activity of the enzyme having L-AHG as a substrate in the sample fractioned from the crude extract was measured as explained below. First, 10 μl of fraction sample was input into 200 μl of reaction solution (20 mM of Tris-HCl and pH 8.0) containing 5 mM of several cofactors (NAD, NADP, and ATP) and 5 mM of substrate (L-AHG) and reacted for 30 mM at 25° C. The final reaction solution was confirmed by measuring a final concentration of NAD(P)H transformed at 339 nm according to End-point UV-methods using a microplate spectrophotometer (Bio-Tek Instruments, Inc.) (FIG. 1), or generation of the reaction product was confirmed with TLC.

Example 2

Identification of an Active Protein

After active fractions were developed with SDS-PAGE, a size of proteins included in the active fractions was comparably confirmed using an Image J program. As a result, the size of proteins in which same increase was shown in the section having increasing activity was confirmed to be about 52 kDa. Dehydrogenase having a similar size using NAD(P) was searched in the National Center for Biotechnology Information (NCBI)'s site (http://www.ncbi.nlm.nih.gov/) among genome sequences of Sde. As a result, it was predicted as EMBL ID ABD81905 (hereinafter referred to as 'L-AHG dehydrogenase,' 'AHGD'), and sequences of proteins having sequence homology thereof were confirmed. Activity of AHGD derived from Sde and *P. atlantica* T6c (hereinafter, referred to as 'Patl') was finally verified by cloning explained below.

(Cloning of AHGD)

Oligonucleotides were produced based on information about a nucleotide sequence of AHGD obtained from *S. degradans* and *P. atlantica* genome sequences (European Molecular Biology Laboratory (EMBL) sequence database identification numbers: CP000282, 1446 nt and CP000388, 1464 nt).

```
1. Sdc;
                                                            (SEQ ID NO: 9)
primer 1: 5'-GGCGGTGGTGGCGGCATGAAAATTCATAACATGAAAAATTTTATCAACG-3'(49 mer)

                                                           (SEQ ID NO: 10)
primer 2: 5'-GTTCTTCTCCTTTGCGCCCCTATCATTCAGCAAAATACACTGTCTTC-3' (47 mer)

2. Patl;
                                                           (SEQ ID NO: 11)
primer 1: 5'-GGCGGTGGTGGCGGCATGACTGTTCAAGATTTACACTTTAAAAACAA-3'(47 mer),

                                                           (SEQ ID NO: 12)
primer 2: 5'-GTTCTTCTCCTTTGCGCCCCTACTAAGCCTCATTGATATAAACGGTT-3'(47 mer).
```

Figure 5:
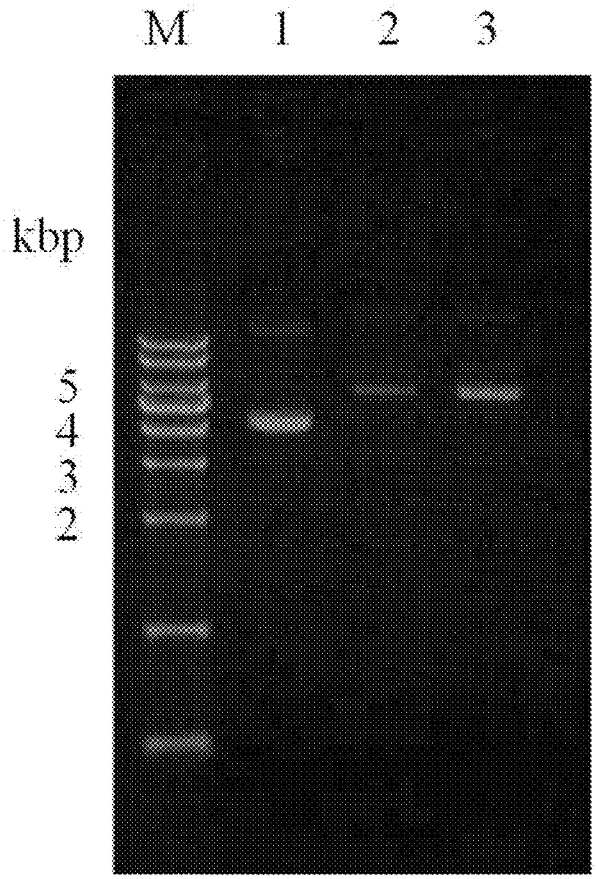
FIG. 5 illustrates a PCR product of sdeAHGD and patlAHGD of the invention, in which M indicates a 1 kb marker, lane 1 indicates a pB2 vector, lane 2 indicates patlAHGD, and lane 3 indicates sdeAHGD.
Figure 6:
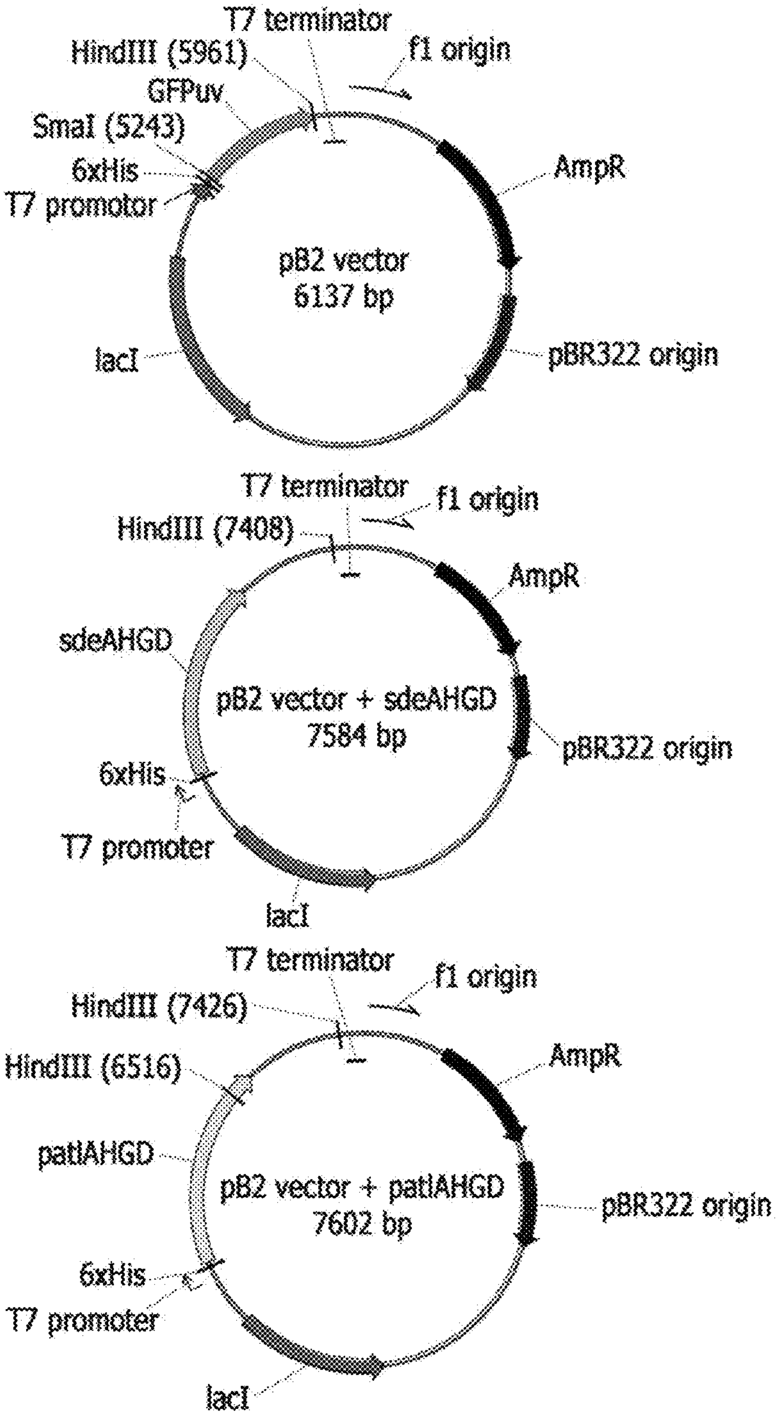
FIG. 6 illustrates cleavage maps of an expression vector of the invention.

Target genes were amplified using Sde and Patl genomic DNA with a polymerase chain reaction (PCR) (hereinafter referred to as '*S. degradans*: sdeAHGD' and '*P. atlantica*: patlAHGD'). FIGS. 3 and 4 show amplified sdeAHGD and patlAHGD amino acid sequences and FIG. 5 shows PCR products thereof. Amplified sdeAHGD and patlAHGD DNA fragments were cloned to transform a pET21a (hereinafter referred to as 'pB2') vector having six histidine residues at an amino terminal, and then were expressed by transformation with *E. coli* BL21 (DE3) for expression (FIG. 6).

(Expression and Purification of AHGD)

Figure 7:
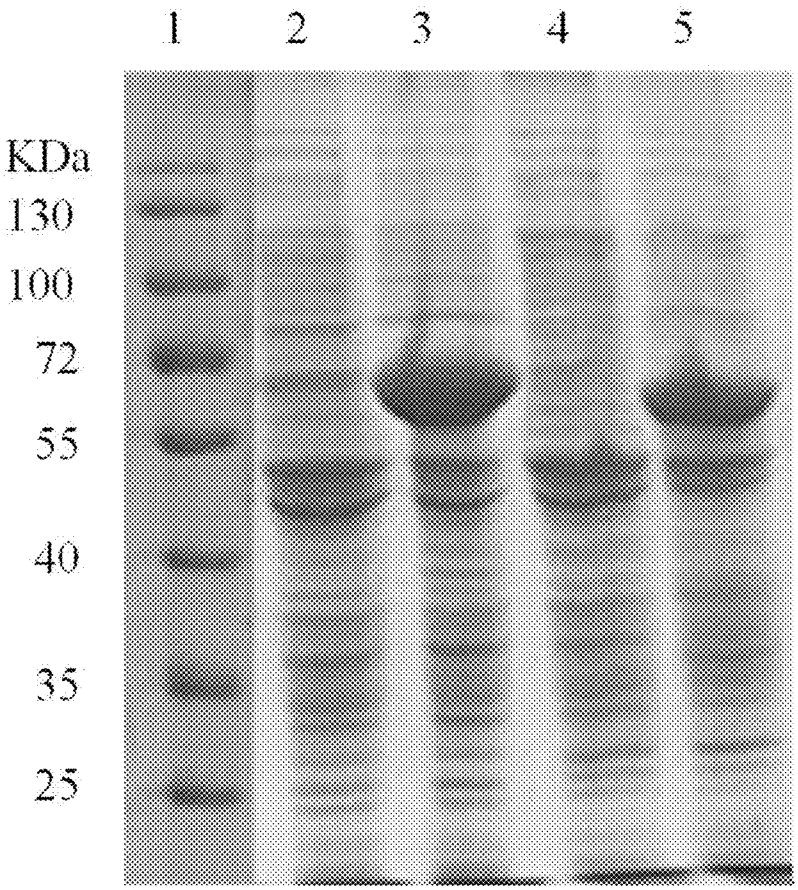
FIG. 7 illustrates an analysis result of 10% of SDS-PAGE of SdeAHGD and PatlAHGD proteins of the invention, in which lane 1 indicates a molecular size marker, lane 2 indicates SdeAHGD before expression, lane 3 indicates SdeAHGD after expression, lane 4 indicates PatlAHGD before expression, and lane 5 indicates PatlAHGD after expression.

In order to check expressions of SdeAHGD and PatlAHGD in the transformed *E. coli*, the transformed *E. coli* BL21 (DE3) containing recombinant sdeAHGD and patlAHGD genes was inoculated in a Luria-Bertani (LB) medium containing 50 mg/L of ampicillin antibiotic and then incubated with shaking at 37° C. until $OD_{600}$=0.5 to 1.0. Then, IPTG with a concentration of 0.5 mM/L was added and expression was induced for 24 hours at 16° C. and 180 rpm. The culture broth was centrifuged for 10 min at 4000 rpm to recover the biomass. The recovered biomass was subjected to the crude extract using the sonicator and separated into a crude enzyme solution and sediment by centrifuging for 60 min at 4° C. and 15000 rpm. The crude enzyme solution was filtered with a 0.45 μm filter paper (Sartorius Stedim Biotech, Germany), and then purified by affinity chromatography using a Histaq column (GE Healthcare, USA), and purified again by ion exchange chromatography using a Hitraq Q column. The eluted active fractions were applied to the buffer solution (20 mM of Tris-HCl and pH 8.0) using a desalting column. The expressed SdeAHGD and PatlAHGD were confirmed by 10% of SDS-PAGE analysis (FIG. 7).

Experimental Example 2

Confirmation of AHGD Activity

The purified protein activity was analyzed under the following conditions. First, SdeAHGD and PatlAHGD enzymes (final concentration of 0.1 mg/mL) were respectively input into 200/JA of reaction solution (20 mM of Tris-HCl and pH 8.0) containing 5 mM of cofactor (nicotinamide adenine dinucleotide phosphate, NADP) and 5 mM of substrate (L-AHG) and reacted for 1 to 190 min at 25° C.

Figure 8:
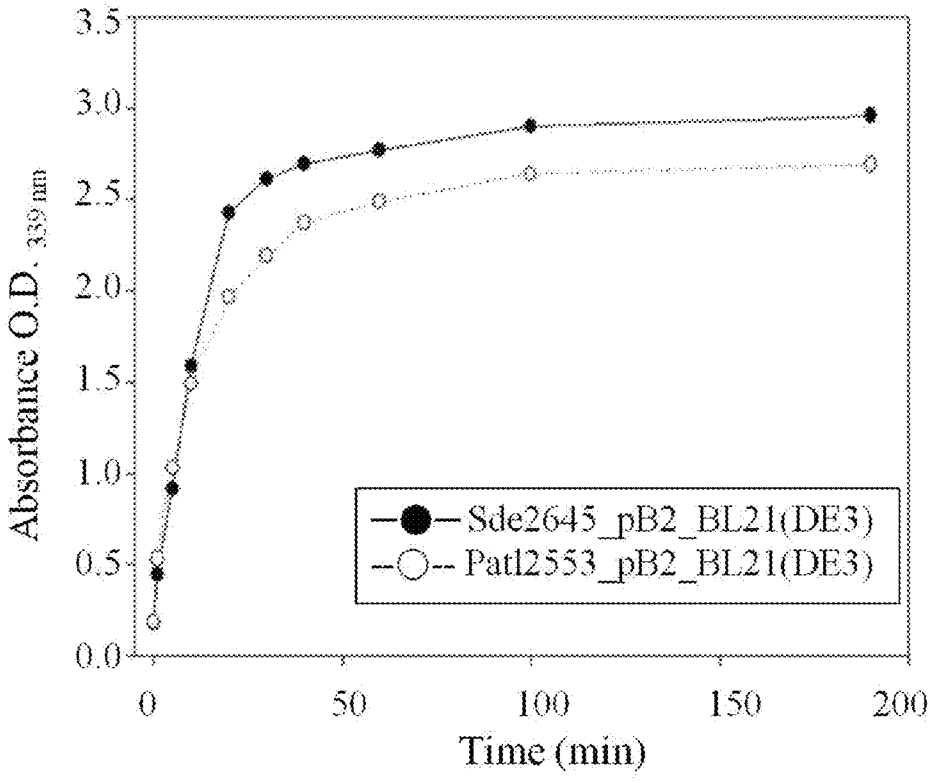
FIG. 8 illustrates enzyme activities of SdeAHGD and PatlAHGD of the invention with respect to L-AHG.

In the reaction solution, final concentrations of converted NADPH were measured at 339 nm per unit time according to Endpoint UV methods using a microplate spectrophotometer (Bio-Tek Instruments, Inc.) (FIG. 8).

Figure 9:
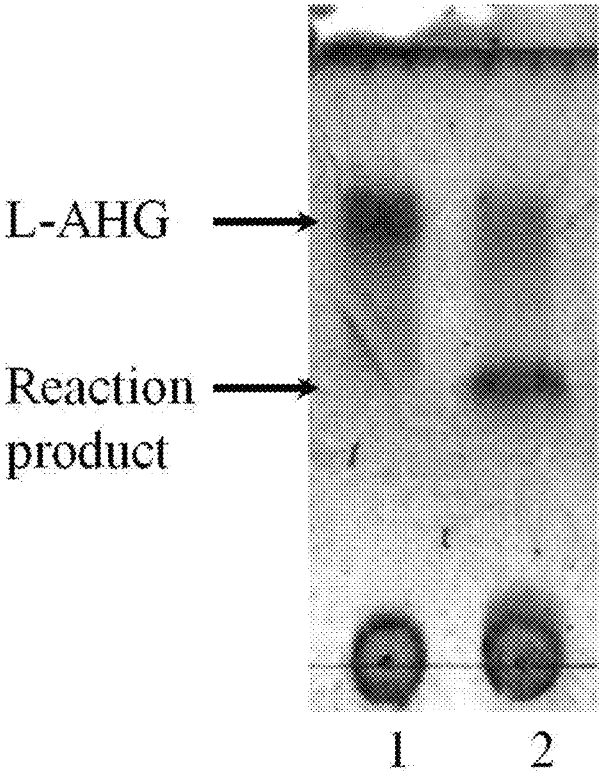
FIG. 9 illustrates a reaction product of enzyme activity, in which lane 1 indicates L-AHG and lane 2 indicates a reaction product.

The reaction product according to AHGD enzyme activity was confirmed using a thin layer chromatography (TLC) method. In the confirmation with TLC, 1 μl of reaction solution was dripped on a silica gel 60 TLC plate and was developed in TLC solvent conditions (n-Butanol:EtOH:water=3:2:2). The developed TLC plate was dried after treatment with a primary treatment solution of sulfuric acid (10% (v/v) $H_2SO_4$ in ethanol) and the primarily treated plate was heated after treatment with a second treatment solution of naphthoresorcinol (0.2% (w/v) naphthoresorcinol in ethanol) (FIG. 9).

Experimental Example 3 pH Effect on Enzyme Activity

In order to check optimal pH of the AHGD enzyme, an activity of the enzyme was measured in the range of pH 3 to 11. The buffer solutions with respect to each pH include: 20 mM of a citric acid buffer solution for pH 3 to 5.5; 20 mM of a sodium phosphate buffer solution for pH 5.5 to 7.0; 20 mM of a Tris-HCl buffer solution for pH 7.0 to 9.0; and 20 mM of a borate buffer solution for pH 9.0 to 11.0. Each buffer solution containing 2 mM of substrate (L-AHG) and 1.5 mM of cofactor (NADP) with final enzyme protein concentration of 0.1 mg/mL was reacted for 15 min at 25° C. In order to stop reaction of the enzyme, the enzyme was treated for 5 min at 95° C., centrifuged for 5 min at 12000 rpm, and then the converted NADPH was measured at 339 nm according to End-point UV-methods.

Figure 10:
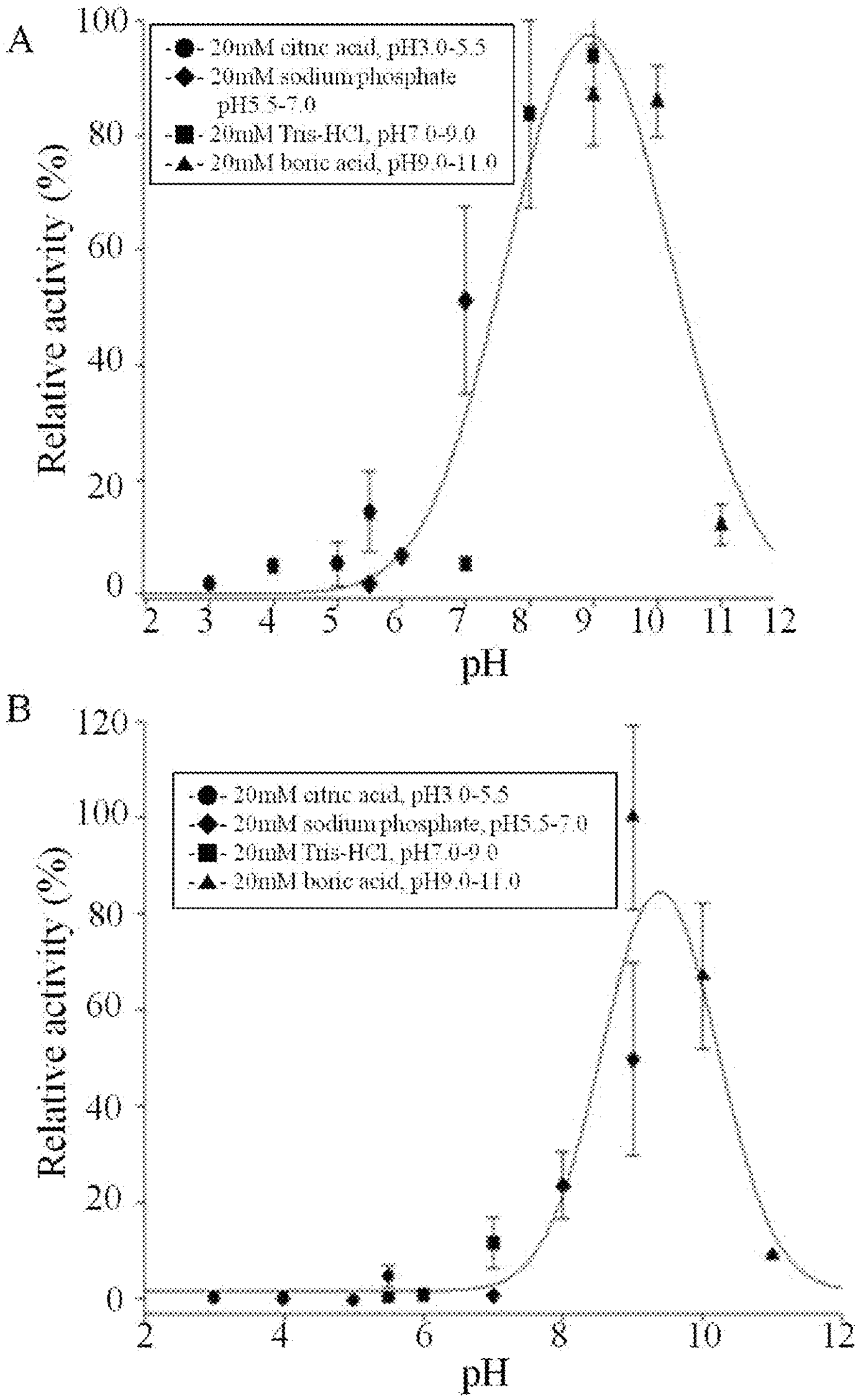
FIG. 10 illustrates a pH effect on SdeAHGD and PatlAHGD activities of the invention, in which A indicates SdeAHGD and B indicates PatlAHGD.

As illustrated in FIG. 10, the activity of SdeAHGD was highest in the buffer solution (20 mM of Tris-HCl and pH 9.0) and the activity of PatlAHGD was highest in the buffer solution (20 mM of borate and pH 9.0).

Experimental Example 4

Temperature Effect on Enzyme Activity

In order to check optimal temperature of AHGD enzyme, each AHGD activity was measured in the range of 4, 16, 25, 37, 50, 70, and 90° C. SdeAHGD was measured in the buffer solution (20 mM of borate and pH 9.0) and PatlAHGD was measured in the buffer solution (20 mM of Tris-HCl and pH 9.0). Each buffer solution containing 2 mM of substrate (L-AHG) and 1.5 mM of cofactor (NADP) with a final enzyme protein concentration of 0.1 mg/mL was reacted for 15 min at the predetermined temperatures. In order to stop reaction of the enzyme, the enzyme was treated for 5 min at 95° C., centrifuged for 5 min at 12000 rpm, and then the converted NADPH was measured at 339 nm according to End-point UV-methods.

Figure 11:
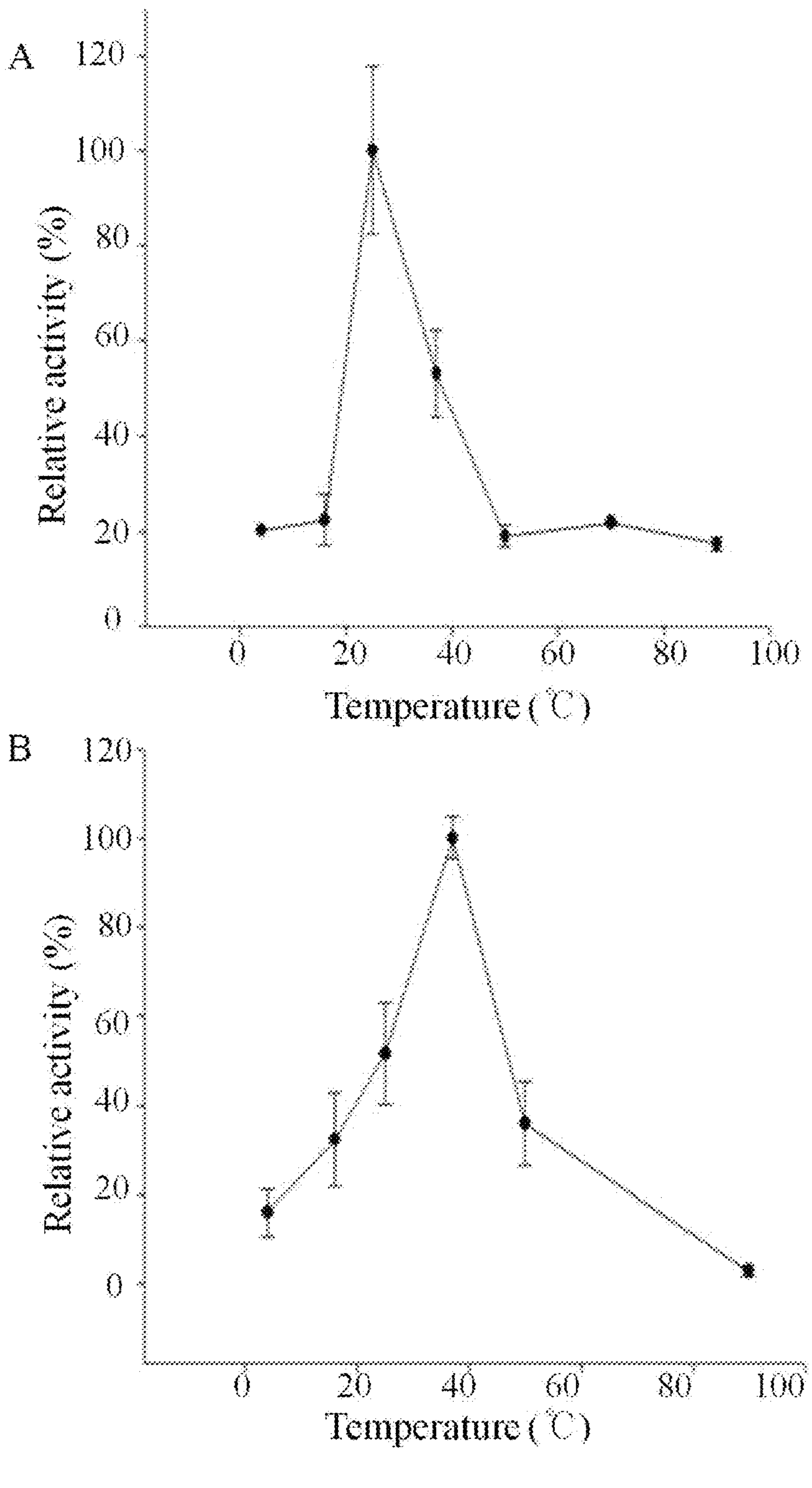
FIG. 11 illustrates a temperature effect on SdeAHGD and PatlAHGD activities of the invention, in which A indicates SdeAHGD and B indicates PatlAHGD.

As illustrated in FIG. 11, SdeAHGD showed the best activity at 25° C. and PatlAHGD showed the best activity at 37° C.

Experimental Example 5

Kinetic Analysis of Enzyme

Final protein concentrations of SdeAHGD and PatlAHGD were fixed to 0.1 mg/mL for kinetic analysis. SdeAHGD includes a substrate (L-AHG, 21 mg/mL) of 1.8, 2.0, 2.2, 2.5, 2.8 μl and PatlAHGD includes a substrate (L-AHG, 21 mg/mL) of 1.5, 1.8, 2.0, 2.2, 2.5 μl). Buffer solutions (SdeAHGD: 20 mM of borate and pH 9.0, and PatlAHGD: 20 mM of Tris-HCl and pH 9.0) containing 1.5 mM of cofactor (NADP) were used. The enzyme reaction of SdeAHGD was reacted for 15 min at 25° C. and the enzyme reaction of PatlAHGD was reacted for 10 min at 25° C. In order to stop reaction of the enzyme, the enzyme was treated for 5 min at 95° C., and then the converted NADPH was measured at 339 nm according to End-point UV-methods by taking a supernatant which was obtained by centrifuging for 5 min at 12000 rpm.

As illustrated in FIG. 12, $K_m$ values of SdeAHGD and PatlAHGD were confirmed as 1.2202 and 2.8529, and $K_{cat}$ values of SdeAHGD and PatlAHGD were confirmed as 15.0376 and 51.5464.

Example 3

Purification and Confirmation of Reaction Product

Figure 13:
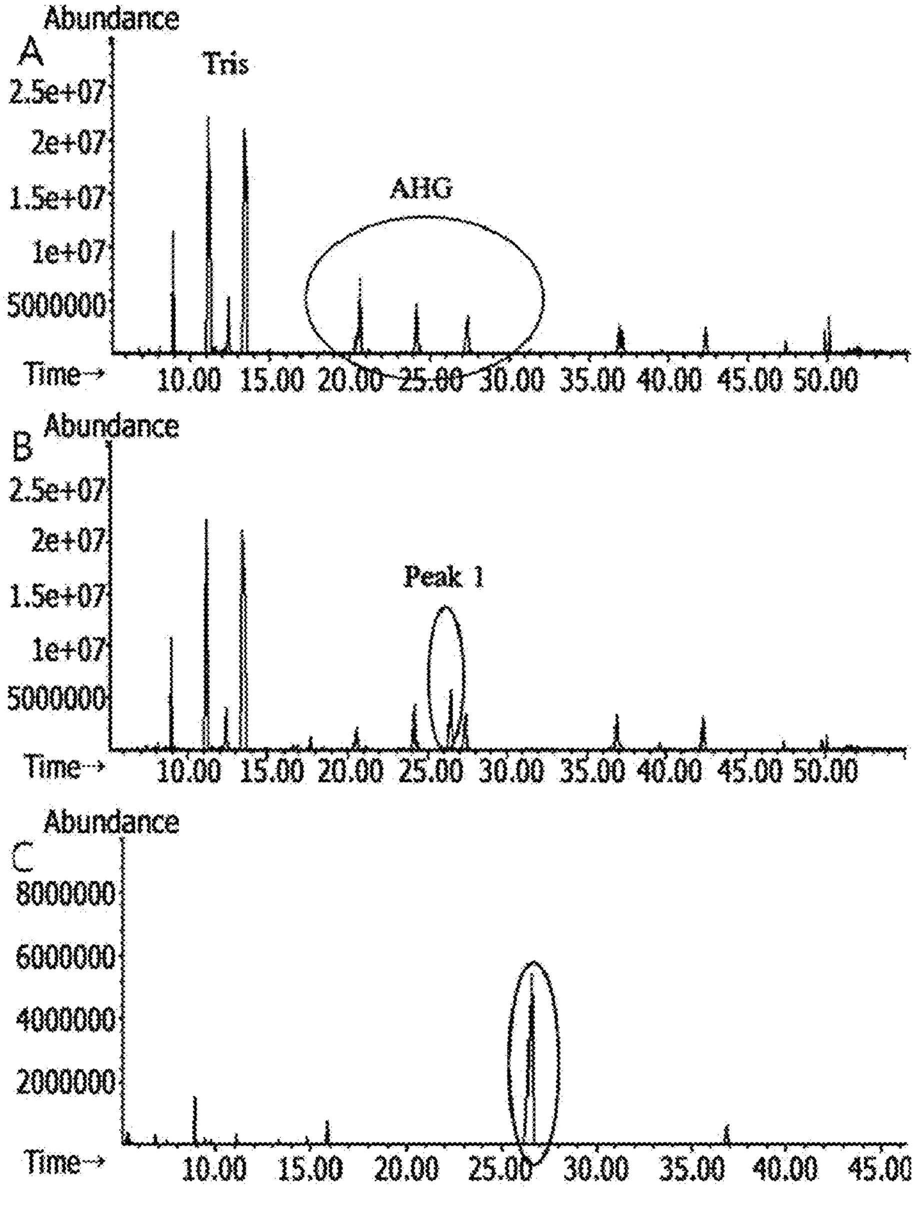
FIG. 13 illustrates a GC/MS total ion chromatogram, in which A indicates a reaction product before enzyme activity, B indicates a reaction product after enzyme activity, and C indicates a reaction product of enzyme activity after fractional crystallization.
Figure 14:
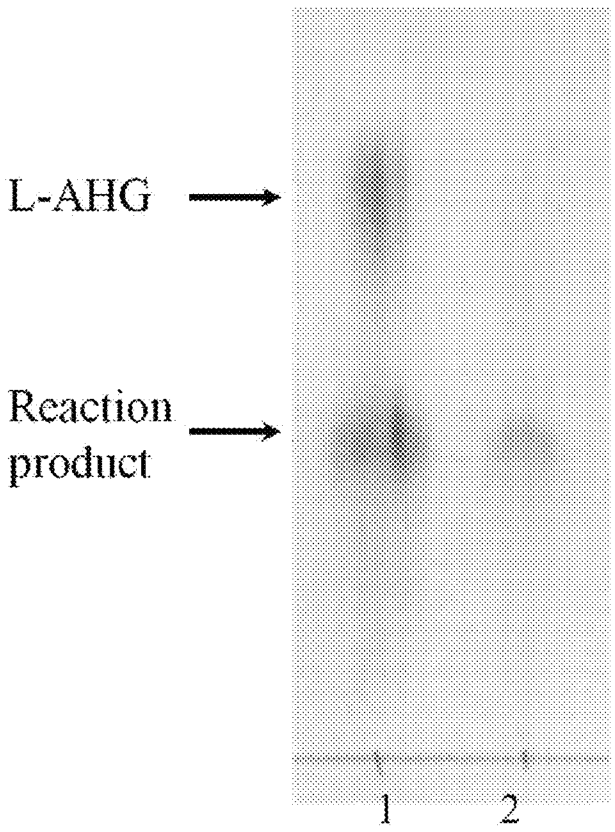
FIG. 14 illustrates thin layer chromatography (TLC) of reaction products before and after fractional crystallization, in which lane 1 indicates a reaction product before fractional crystallization and lane 2 indicates a reaction product after fractional crystallization.

Dried mixtures were extracted based on differences in polarity using solvent extraction methods and only the reaction product was finally purified. The specific experimental methods are given below. The dried reaction product was suspended in methanol, which is a polar solvent, and then only a portion of supernatant dissolved in the solvent was taken by centrifuging and dried again. Due to differences in polarity, L-AHG and a reaction product were dissolved in methanol but NADP and Tris-HCl were relatively insoluble. In order to separate L-AHG and the reaction product, the re-dried reaction product was re-suspended in butanol, which is a solvent having a lower polarity than methanol. At this time, the supernatant portion in which L-AHG was dissolved was removed and the sediment portion was dried again. In order to obtain a reaction product having a high purity, the above-described treatments were repeated three times. Then, the dried reaction product was dissolved in tertiary distilled water and the purity was confirmed with GC/MS (FIG. 13) and TLC (FIG. 14).

Experimental Example 6

NMR Analysis of Activity Product

Figure 15:
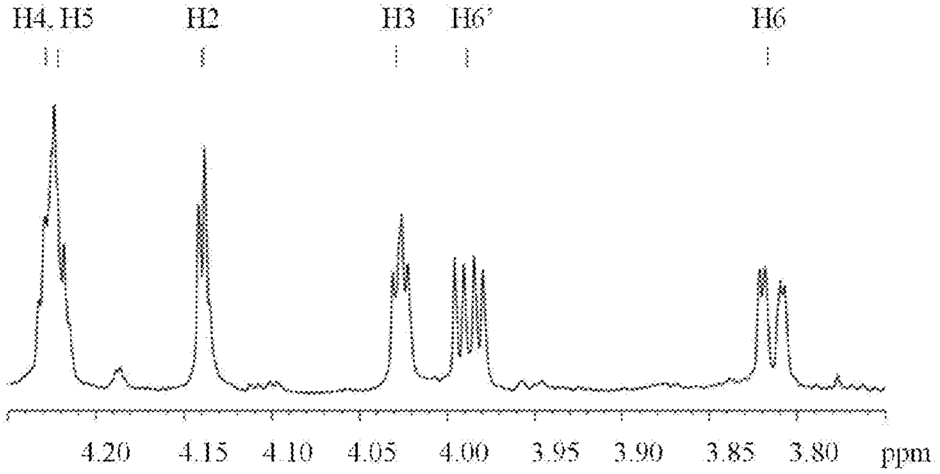
FIG. 15 illustrates an NMR spectrum result of a purified reaction product in which 3-(trimethylsilyl)propionic-2,2,3,3-$d_4$acid is used as an internal standard material.

In order to identify a purified reaction product, NMR analysis was performed. The dried reaction product was dissolved in $D_2O$, $^1H$ chemical shift was determined based on 3-(trimethylsilyl)propionic-2,2,3,3-$d_4$ acid, and the structure of the reaction product was analyzed by 2D heteronuclear single quantum coherence ($^1H$-$^{13}C$HSQC) and 2D heteronuclear multiple bond correlation ($^1H$-$^{13}C$HMBC) spectra. FIG. 15 illustrates an analysis result of $^1H$ chemical shift.

As illustrated in FIG. 15, the hydrogen bond in an aldehyde group on C1 of L-AHG used as a substrate in the enzyme reaction was not shown in the reaction product. As a result, it was understood that a change in the functional group on C1 had occurred.

2D NMR analysis was performed to find a specific structural change and identification.

Figure 16:
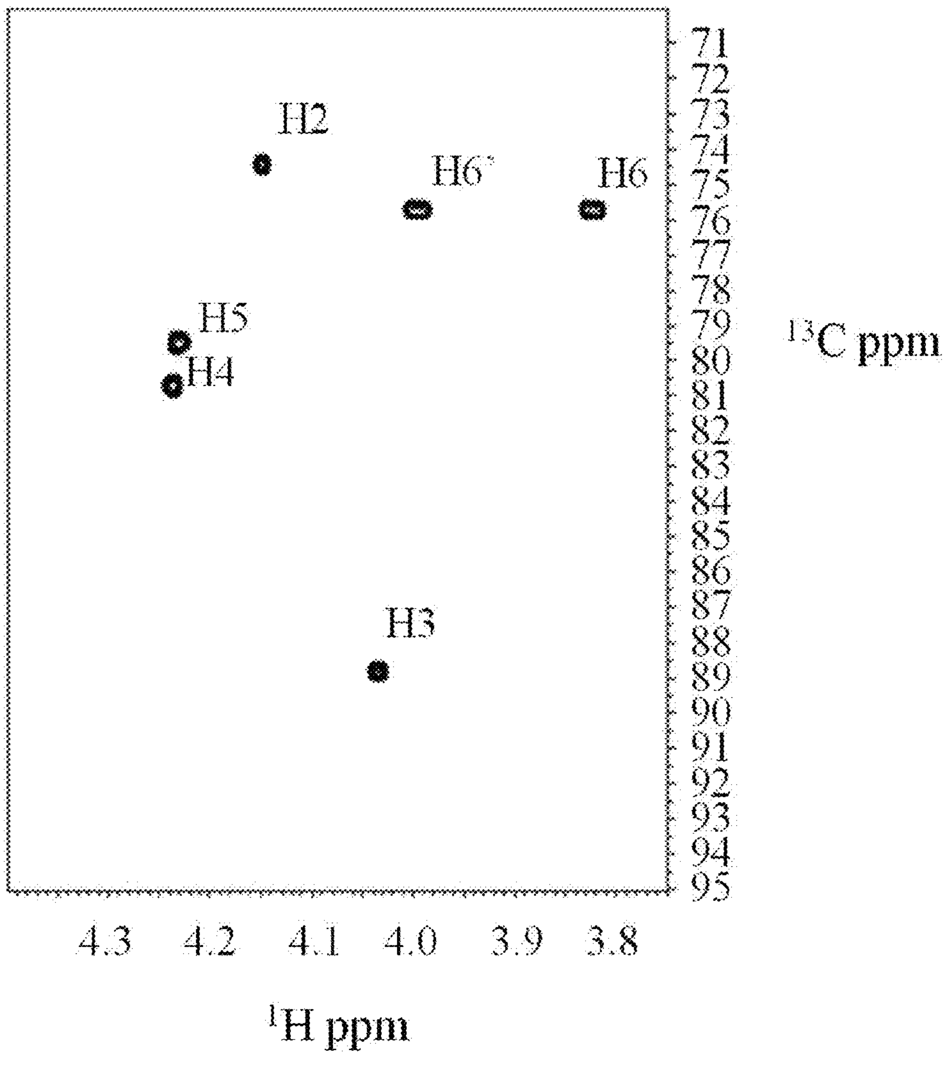
FIG. 16 illustrates a 2D$^1$H-$^{13}$CHSQC spectrum of the purified reaction product.

FIG. 16 illustrates a result of hydrogen-carbon pairs shown through 2D $^1H$-$^{13}C$HSQC and shows six H—C pairs. It was found that 1H—C pair which has been present in L-AHG had disappeared.

Figure 17:
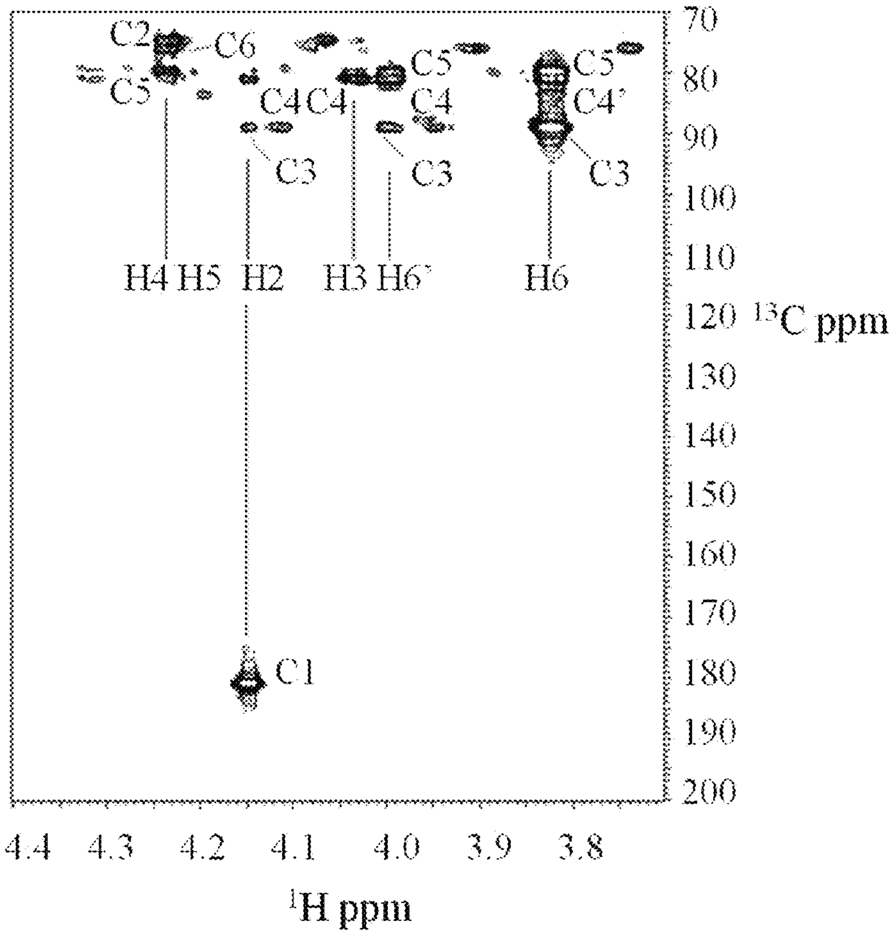
FIG. 17 illustrates a 2D$^1$H-$^{13}$CHMBC spectrum of the purified reaction product.

In addition, according to 2D $^1H$-$^{13}C$HMBC analysis in FIG. 17, C3-H6 and C3-H6' bond occurred. Accordingly, it was confirmed that an anhydro circle between C3 and C6 was maintained. Moreover, H2 is associated with 181.5 ppm of carbonyl carbon, and the oxidation reaction in which C1 was oxidized to a carboxyl group occurred. This is consistent with the result in FIG. 16 in which 1H—C bond disappeared.

Figure 18:
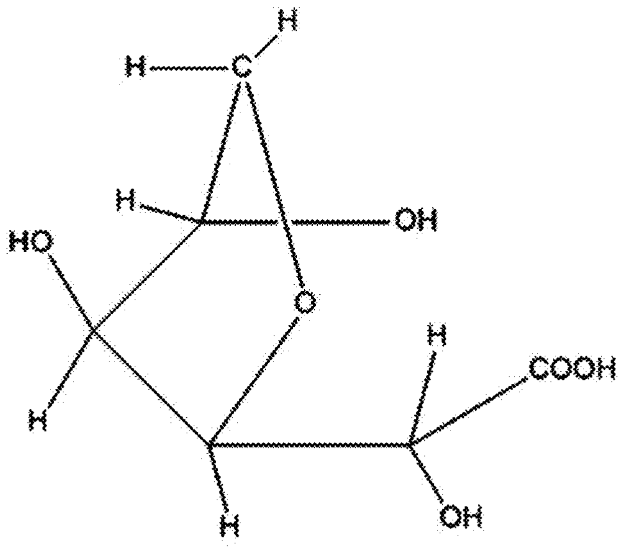
FIG. 18 illustrates a chemical structure of 3,6-anhydro-galatonic acid.

As a result, when the enzyme was reacted with L-AHG as a substrate and NADP as a cofactor, NADP was reduced to NADPH, and accordingly, the oxidation reaction occurred in the substrate. This oxide structure in which an aldehyde group on C1 of L-AHG was oxidized to a carboxyl group was analyzed by NMR. FIG. 18 illustrates a structure of the identified oxide. This oxide is called 3,6-anhydrogalatonic acid according to the most common nomenclature of compounds.

The invention may be used for producing bio-energy with agarose metabolism.

While the invention has been shown and described with reference to predetermined exemplary embodiments thereof, it will be understood by those skilled in the art that various changes in form and details may be made therein without departing from the scope of the invention as defined by the appended claims.

What is claimed is:

1. An isolated cDNA molecule comprising no more than 1461 nucleotides encoding (a) a protein that comprises an amino acid sequence as set forth in any one of SEQ ID NOs: 1 to 4, or (b) a variant of the protein having at least 98% identity to the protein and containing at least one conservative substitution modification relative to the protein.

2. The isolated cDNA molecule of claim 1, wherein the isolated cDNA molecule encodes the protein.

3. The isolated cDNA molecule of claim 1, wherein the isolated cDNA molecule encodes the variant.

4. The isolated cDNA molecule of claim 3, wherein the variant contains only one conservative substitution modification relative to the protein.

5. A recombinant vector comprising the isolated cDNA molecule of claim 2 and a heterologous nucleic acid sequence.

6. A host cell transformed with the recombinant vector of claim 5.

7. A method of producing 3,6-anhydro-L-galactose dehydrogenase which includes a step of obtaining 3,6-anhydro-L-galactose dehydrogenase from a culture of the host cell of claim 6.

* * * * *

```
                     SEQUENCE LISTING


<160> NUMBER OF SEQ ID NOS: 12

<210> SEQ ID NO 1
<211> LENGTH: 481
<212> TYPE: PRT
<213> ORGANISM: Saccharophagus degradans 2-40

<400> SEQUENCE: 1

Met Lys Ile His Asn Met Lys Asn Phe Ile Asn Gly Glu Tyr Ile Ala
1               5                   10                  15

Ser Gln Ala Asp Gly Ala Ile Asp Val Leu Ser Pro Ser Thr Gly Lys
            20                  25                  30

Lys Val Gly Asp Ile Pro Ala Gly Cys Val Glu Asp Ala Gln Leu Ala
        35                  40                  45

Leu Asp Thr Ala Asn Ala Ala Gln Lys Leu Trp Ala Lys Lys Thr Asn
    50                  55                  60

Arg Glu Arg Ala Lys Ile Leu Arg Val Phe Ala Ala Asn Ile Arg Ala
65                  70                  75                  80

Ala Ala Asp Asp Leu Ala Lys Leu Leu Val Ser Glu Gln Gly Lys Leu
                85                  90                  95

Leu Ser Val Ala Gln Met Glu Val Glu Ala Thr Ala Thr Phe Ile Glu
            100                 105                 110

Tyr Ala Cys Asp Asn Ala Leu Thr Ile Glu Gly Asp Ile Leu Pro Ser
        115                 120                 125

Asp Asn Pro Asn Glu Lys Ile Tyr Ile His Lys Val Pro Arg Gly Val
    130                 135                 140

Val Val Ala Ile Thr Ala Trp Asn Phe Pro Leu Ala Leu Ala Gly Arg
145                 150                 155                 160

Lys Ile Gly Pro Ala Leu Val Thr Gly Asn Ala Ile Val Val Lys Pro
                165                 170                 175

Thr Gln Glu Thr Pro Leu Ala Thr Leu Ala Leu Gly Glu Leu Ala Asn
            180                 185                 190

Ala Ala Gly Ile Pro Ala Gly Val Leu Asn Ile Val Asn Gly Arg Gly
        195                 200                 205

Ser Val Val Gly Gln His Leu Cys Glu Ser Pro Ile Thr Arg Leu Ile
    210                 215                 220

Thr Met Thr Gly Ser Thr Pro Ala Gly Gln Arg Ile Tyr Arg Thr Ser
225                 230                 235                 240

Ala Asp His Leu Thr Pro Val Met Leu Glu Leu Gly Gly Lys Ala Pro
                245                 250                 255

Phe Ile Val Met Glu Asp Ala Asn Leu Glu Ser Ala Val Glu Ala Ala
            260                 265                 270

Phe Thr Thr Arg Tyr Ala Asn Cys Gly Gln Val Cys Thr Cys Ala Glu
        275                 280                 285

Arg Leu Tyr Val His Glu Ser Ile Tyr Pro Ala Phe Met Asp Lys Leu
    290                 295                 300
```

-continued

```
Leu Glu Lys Val Lys Ala Ile Lys Val Gly Asp Pro Met Ala Ala Asp
305                 310                 315                 320

Thr Asp Met Gly Pro Lys Val Asn Gln Ser Glu Ile Glu Asn Ile Asp
                325                 330                 335

Ala Leu Val Lys Lys Gly Ile Glu Gln Gly Ala Thr Leu Leu His Gly
            340                 345                 350

Gly Lys Arg Ala His Val Pro Gly Phe Glu Gly Gly Asn Trp Tyr Glu
        355                 360                 365

Pro Thr Leu Leu Gly Asp Val Gln Gln Ser Asn Ile Leu Val His Glu
    370                 375                 380

Glu Thr Phe Gly Pro Ile Leu Pro Val Val Lys Ile Asn Ser Ile Glu
385                 390                 395                 400

Gln Ala Ile Glu Tyr Thr Asn Asp Ser Glu Tyr Gly Leu Ser Thr Tyr
                405                 410                 415

Leu Phe Thr Gln Asn Leu Lys Tyr Ile His Gln Tyr Ile Ala Glu Val
            420                 425                 430

Glu Ala Gly Glu Val Tyr Val Asn Arg Gly Ile Gly Glu Gln His Gln
        435                 440                 445

Gly Phe His Asn Gly Trp Lys Leu Ser Gly Ala Gly Gly Glu Asp Gly
    450                 455                 460

Arg Tyr Gly Leu Glu Gln Tyr Leu Glu Lys Lys Thr Val Tyr Phe Ala
465                 470                 475                 480

Glu


<210> SEQ ID NO 2
<211> LENGTH: 487
<212> TYPE: PRT
<213> ORGANISM: Pseudoalteromonas atlantica

<400> SEQUENCE: 2

Met Thr Val Gln Asp Leu His Phe Lys Asn Lys Val Asn Phe Ile Gly
1               5                   10                  15

Gly Gln Tyr Val Pro Ser Asn Glu Ser Asp Thr Ile Asp Ile Leu Ser
            20                  25                  30

Pro Ser Thr Gly Lys Val Ile Gly Glu Ile Pro Ala Gly Cys Lys Ala
        35                  40                  45

Asp Ala Glu Asn Ala Leu Glu Val Ala Gln Ala Ala Gln Lys Ala Trp
    50                  55                  60

Ala Lys Leu Thr Ala Arg Thr Arg Gln Asn Met Leu Arg Thr Phe Ala
65                  70                  75                  80

Asn Lys Ile Arg Glu Asn Lys His Ile Leu Ala Pro Met Leu Val Ala
                85                  90                  95

Glu Gln Gly Lys Leu Leu Ser Val Ala Glu Met Glu Val Asp Val Thr
            100                 105                 110

Ala Thr Phe Ile Asp Tyr Gly Cys Asp Asn Ala Leu Thr Ile Glu Gly
        115                 120                 125

Asp Ile Leu Pro Ser Asp Asn Gln Asp Glu Lys Ile Tyr Ile His Lys
    130                 135                 140

Val Pro Arg Gly Val Val Val Gly Ile Thr Ala Trp Asn Phe Pro Leu
145                 150                 155                 160

Ala Leu Ala Gly Arg Lys Ile Gly Pro Ala Leu Ile Thr Gly Asn Thr
                165                 170                 175

Met Val Leu Lys Pro Thr Gln Glu Thr Pro Leu Ala Thr Thr Glu Leu
            180                 185                 190
```

-continued

```
Gly Arg Ile Ala Lys Glu Ala Gly Leu Pro Asp Gly Val Leu Asn Val
        195                 200                 205

Ile Asn Gly Thr Gly Ser Val Val Gly Gln Thr Leu Cys Glu Ser Pro
    210                 215                 220

Ile Thr Lys Met Ile Thr Met Thr Gly Ser Thr Val Ala Gly Lys Gln
225                 230                 235                 240

Ile Tyr Lys Thr Ser Ala Glu Tyr Met Thr Pro Val Met Leu Glu Leu
                245                 250                 255

Gly Gly Lys Ala Pro Met Val Val Met Asp Asp Ala Asp Leu Asp Lys
            260                 265                 270

Ala Ala Glu Asp Ala Leu Trp Gly Arg Phe Ala Asn Cys Gly Gln Val
        275                 280                 285

Cys Thr Cys Val Glu Arg Leu Tyr Val His Ala Ser Val Tyr Asp Glu
    290                 295                 300

Phe Met Ala Lys Phe Leu Pro Leu Val Lys Gly Leu Lys Val Gly Asp
305                 310                 315                 320

Pro Met Asp Ala Asp Ser Gln Met Gly Pro Lys Cys Asn Gln Arg Glu
                325                 330                 335

Ile Asp Asn Ile Asp His Ile Val His Glu Ala Ile Lys Gln Gly Ala
            340                 345                 350

Thr Val Ala Thr Gly Gly Lys Thr Ala Thr Val Glu Gly Phe Glu Gly
        355                 360                 365

Gly Cys Trp Tyr Glu Pro Thr Val Leu Val Asp Val Lys Gln Asp Asn
    370                 375                 380

Ile Val Val His Glu Glu Thr Phe Gly Pro Ile Leu Pro Ile Val Lys
385                 390                 395                 400

Val Ser Ser Met Glu Gln Ala Ile Glu Phe Cys Asn Asp Ser Ile Tyr
                405                 410                 415

Gly Leu Ser Ala Tyr Val His Thr Gln Ser Phe Ala Asn Ile Asn Gln
            420                 425                 430

Ala Ile Ser Asp Leu Glu Val Gly Glu Val Tyr Ile Asn Arg Gly Met
        435                 440                 445

Gly Glu Gln His Gln Gly Phe His Asn Gly Trp Lys Gln Ser Gly Phe
    450                 455                 460

Gly Gly Glu Asp Gly Lys Phe Gly Leu Glu Gln Tyr Leu Glu Lys Lys
465                 470                 475                 480

Thr Val Tyr Ile Asn Glu Ala
                485


<210> SEQ ID NO 3
<211> LENGTH: 486
<212> TYPE: PRT
<213> ORGANISM: Microscilla sp. PRE1

<400> SEQUENCE: 3

Met Ile Met Ser Thr Val Lys Asn Tyr Lys Leu Tyr Ile Asp Gly Glu
1               5                   10                  15

Trp Ile Asp Ala Thr Thr Gly Glu Ser Gln Glu Ile Leu Ser Pro Thr
            20                  25                  30

Asp Glu Thr Val Val Gly Thr Val Gln Met Gly Val Glu Ala Asp Ala
        35                  40                  45

Gln Ile Ala Leu Glu Ala Ala Glu Arg Ala Gln Lys Gln Trp Lys Lys
    50                  55                  60

Val Pro Ala Arg Lys Arg Ala Asp Leu Leu Arg Thr Phe Ala Ala Glu
65                  70                  75                  80
```

-continued

```
Ile Lys Ala Asn Lys Asn Gln Leu Ala Glu Leu Leu Val Arg Glu Gln
                85                  90                  95

Gly Lys Leu Leu Ala Val Ala Lys Met Glu Val Glu Val Thr Ala Ser
            100                 105                 110

Phe Ile Glu Tyr Ala Cys Asp Gly Ala Arg Ser Ile Glu Gly Asp Ile
        115                 120                 125

Ile Pro Ser Asp Asn Pro Ala Glu His Ile Met Ile His Lys Ile Pro
    130                 135                 140

Arg Gly Val Val Val Ala Ile Thr Ala Trp Asn Phe Pro Leu Ala Leu
145                 150                 155                 160

Ala Gly Arg Lys Leu Gly Pro Ala Leu Val Ala Gly Asn Ser Val Val
                165                 170                 175

Leu Lys Pro Thr Gln Glu Thr Pro Ile Ala Thr Leu Glu Leu Gly Asn
            180                 185                 190

Ile Ala Asn Lys Val Gly Leu Pro Lys Gly Leu Ile Asn Ile Leu Thr
        195                 200                 205

Gly Gln Gly Ser Val Leu Gly Asn Ala Leu Val Ala Asn Pro Ile Thr
    210                 215                 220

Lys Met Val Ser Met Thr Gly Ser Thr Pro Ala Gly Gln Gln Ile Phe
225                 230                 235                 240

Arg Thr Ala Ala Glu Asn Leu Ile His Val Gln Leu Glu Leu Gly Gly
                245                 250                 255

Lys Ala Pro Cys Ile Val Phe Asp Asp Ala Asp Leu Glu Gln Ala Val
            260                 265                 270

Glu Gly Ala Phe His Ser Arg Phe Asp Asn Cys Gly Gln Val Cys Thr
        275                 280                 285

Ser Asn Glu Arg Leu Tyr Val His Glu Ser Ile Tyr Asn Glu Phe Met
    290                 295                 300

Glu Arg Phe Met Glu Lys Val Lys Gly Leu Lys Leu Gly Asn Pro Met
305                 310                 315                 320

Asp Ala Ala Thr Thr Ile Gly Pro Lys Val Asn Ala Lys Glu Val Ala
                325                 330                 335

His Met Glu His Leu Val Thr Lys Ser Val Glu Glu Gly Ala Thr Val
            340                 345                 350

Ala Ile Gly Gly Lys Lys Pro Gln Gly Lys Ala Phe Glu Lys Gly His
        355                 360                 365

Trp Phe Glu Pro Thr Ile Leu Thr Asp Val Lys Gln Asn Met Thr Ile
    370                 375                 380

Val His Glu Glu Ser Phe Gly Pro Ile Leu Pro Val Ile Lys Phe Ser
385                 390                 395                 400

Glu Phe Asn Glu Val Ile Gly Tyr Ala Asn Asp Cys Glu Tyr Gly Leu
                405                 410                 415

Ala Ala Met Val Phe Thr Asn Asp Met Asn Lys Ile Met Arg Leu Asn
            420                 425                 430

Asp Glu Leu Glu Phe Gly Glu Ile Tyr Ile Asn Arg Gly His Gly Glu
        435                 440                 445

Gln His Gln Gly Phe His Asn Gly Tyr Lys Leu Ser Gly Thr Gly Gly
    450                 455                 460

Glu Asp Ser Lys Tyr Gly Phe Glu Gln Tyr Met Glu Lys Lys Thr Phe
465                 470                 475                 480

Tyr Ile Lys Tyr Lys Ala
                485
```

<210> SEQ ID NO 4
<211> LENGTH: 486
<212> TYPE: PRT
<213> ORGANISM: Coraliomargarita akajimensis

<400> SEQUENCE: 4

```
Met Ser Thr Asp Thr Ile Thr Ala Tyr Gln Met Tyr Ile His Gly Glu
1               5                   10                  15

Trp Val Asp Ala Thr Ser Gly Lys Ile Val Glu Val Glu Asn Pro Ser
            20                  25                  30

Asn Glu Ala Val Ile Ala Thr Val Gln Asp Gly Asp Ala Ala Asp Ala
        35                  40                  45

Glu Arg Ala Leu Gln Ser Ala Lys Gln Ala Gln Pro Ala Trp Ala Ala
    50                  55                  60

Ile Pro Ala Val Glu Arg Gly Asn Val Leu Ile Lys Phe Ala Asp Leu
65                  70                  75                  80

Ile Lys Ala Asn Arg Glu Arg Leu Ala Arg Leu Leu Ser Ile Glu Met
                85                  90                  95

Gly Lys Thr Tyr Glu Leu Ala Leu Gly Glu Val Asp Val Ser Ala Asp
            100                 105                 110

Phe Ile Asn Phe Pro Ala Gln Ser Ala Arg Arg Thr Glu Gly Asp Ile
        115                 120                 125

Tyr Ser Ser Asp Leu Pro Asn Glu His Ile Trp Ile His Lys Val Pro
    130                 135                 140

Tyr Gly Val Thr Val Gly Ile Ala Ala Trp Asn Phe Pro Leu Ala Leu
145                 150                 155                 160

Ala Cys Arg Lys Ile Gly Pro Ala Leu Thr Ala Gly Asn Ser Met Val
                165                 170                 175

Val Lys Pro Pro Ser Val Thr Pro Cys Ala Val Leu Glu Leu Gly Lys
            180                 185                 190

Leu Ala Lys Glu Ala Gly Ile Pro Asp Gly Val Leu Asn Ile Val Thr
        195                 200                 205

Gly Gly Gly Ser Thr Met Gly Ser Glu Leu Val Lys Asn Lys Leu Thr
    210                 215                 220

Lys Leu Val Thr Met Thr Gly Ser Thr Lys Thr Gly Gln Gln Ile Phe
225                 230                 235                 240

Lys Asp Ser Ala Asp Asn Leu Thr Ala Val Arg Leu Glu Leu Gly Gly
                245                 250                 255

Lys Ala Pro Phe Ile Leu Leu Glu Asp Gly Asp Val Asp Lys Ala Val
            260                 265                 270

Ser Ala Ala Val Val Ser Arg His Leu Asn Ser Gly Gln Val Cys Thr
        275                 280                 285

Cys Pro Glu Arg Phe Tyr Ile His Glu Lys His Tyr Asp Glu Phe Leu
    290                 295                 300

Ala Lys Tyr Thr Asp Glu Val Lys Lys Leu Thr Ile Gly Asp Pro Leu
305                 310                 315                 320

Asp Pro Ser Thr Asn Ile Gly Pro Lys Val Asn Ala Tyr Glu Thr Glu
                325                 330                 335

Ala Ile Gly Lys Ile Val Asp Lys Ala Ile Glu Gln Gly Ala Ser Leu
            340                 345                 350

Val Cys Gly Gly Lys Arg Pro Glu Gly Ala Gln Tyr Glu Lys Gly His
        355                 360                 365

Trp Tyr Glu Pro Thr Ile Leu Thr Gly Cys Asp Asn Ser Met Asp Val
    370                 375                 380
```

-continued

```
Met Arg Glu Glu Val Phe Gly Val Val Ser Pro Ile Met Lys Ile Ser
385                 390                 395                 400

Ser Tyr Glu Glu Ala Leu Glu Leu Ala Asn Asp Ser Asp Tyr Gly Leu
                405                 410                 415

Ala Ala Phe Leu Phe Thr Lys Asp Met Arg Leu Ile Gln Arg Ala Val
            420                 425                 430

Leu Glu Leu Glu Phe Gly Glu Ile Tyr Val Asn Arg Pro Met Gly Glu
        435                 440                 445

Gln Arg Gln Gly Phe His Asn Gly Tyr Lys Leu Ser Gly Thr Gly Gly
    450                 455                 460

Glu Asp Gly Lys Tyr Gly Tyr Glu Asn Tyr Leu Glu Lys Lys Thr Met
465                 470                 475                 480

Tyr Val Asn Phe Ser Glu
                485
```

<210> SEQ ID NO 5
<211> LENGTH: 1443
<212> TYPE: DNA
<213> ORGANISM: Saccharophagus degradans 2-40

<400> SEQUENCE: 5

```
atgaaaattc ataacatgaa aaattttatc aacggcgaat atatagcttc acaagctgat     60

ggcgctattg atgtgctaag cccaagcacc ggtaaaaagg taggcgatat tcccgcagga    120

tgtgtagagg atgcgcagtt ggcgctggat acagccaacg cagctcaaaa gctgtgggca    180

aaaaaaacga acagagagcg cgcaaaaata ttgcgtgtat tcgctgcgaa tattcgtgcg    240

gcggcggatg atttagccaa gctgttagtg agcgagcagg gtaaattact ttctgttgcg    300

caaatggaag tagaagccac agcaacgttt atagaatacg cgtgtgataa cgcgcttact    360

atagagggcg atattttacc ttccgataac cccaacgaaa aatatatat ccacaaagtg    420

ccacgcggtg tggttgtggc aattaccgct tggaattttc cgttagcact ggcgggcaga    480

aaaataggcc cagcacttgt tacaggcaat gctatcgtgg ttaagccaac ccaagaaacg    540

ccacttgcaa cattggcgtt aggcgagcta gctaatgctg cgggtattcc cgccggcgta    600

ctcaatattg taaacggccg tggcagtgtt gttgggcagc acctgtgcga aagcccaata    660

acccgcttaa taaccatgac cggcagcacc cctgctgggc agcgtattta ccgcaccagt    720

gccgatcatt taacgccagt aatgctagaa ctgggcggta aggcaccatt tatcgtaatg    780

gaagatgcca acttagaaag cgcagtagag gcggcattta ctacgcgtta tgccaattgc    840

gggcaagtgt gtacctgtgc cgagcgcctg tatgtacacg aatctattta ccccgctttt    900

atggataagc tacttgagaa ggtgaaagca ataaaagtgg gcgacccaat ggctgccgat    960

accgatatgg gtcccaaggt taatcaaagc gaaatagaaa atattgatgc gctggttaag   1020

aagggtattg agcaaggcgc aaccttgctg catggcggta agcgcgcgca tgtgcctggc   1080

tttgaaggtg gcaactggta tgaacccaca ctgctaggtg atgtgcagca aagtaatatt   1140

cttgtgcacg aagaaacgtt tgggcctatt ttacctgtag ttaaaattaa cagtattgag   1200

caggctatag agtacaccaa cgacagtgag tatggccttt caacgtattt gtttacgcaa   1260

aaccttaaat atattcatca atatattgcc gaggttgagg ccggtgaggt gtatgttaac   1320

cgcggtattg gtgagcagca ccaaggcttc cacaacggtt ggaagctaag cggcgcaggc   1380

ggtgaagatg gtcgttacgg tttagagcag tacttagaga agaagacagt gtattttgct   1440

gaa                                                                 1443
```

-continued

<210> SEQ ID NO 6
<211> LENGTH: 1461
<212> TYPE: DNA
<213> ORGANISM: PatlAHGD: Pseudoalteromonas atlantica

<400> SEQUENCE: 6

```
atgactgttc aagatttaca ctttaaaaac aaggttaatt tcattggagg gcaatatgtg      60
ccctctaacg aatccgatac aattgacata cttagcccgt caactggcaa agtcataggc     120
gaaataccgg caggttgtaa agcggatgct gaaaatgccc tagaggtggc tcaggccgcg     180
caaaaagcat gggctaaatt aaccgctcgt acacgccaga atatgctgcg taccttcgct     240
aacaaaattc gtgagaataa acacattctt gcccctatgc tcgtcgctga gcaaggcaaa     300
ttgttatcag tagccgaaat ggaagtggac gtaaccgcta cgtttatcga ctacggatgt     360
gacaatgccc tgaccataga aggcgacatt ttgccttcag ataatcagga cgaaaaaata     420
tacattcata aggtaccaag aggcgtggtt gtgggcatta ccgcctggaa tttccctctg     480
gcattagcag gtcgaaaaat tggccctgcg cttattaccg gtaataccat ggtgttaaag     540
cctacccaag aaacgccgct tgcaacgact gagcttgggc gtattgccaa agaagcaggc     600
cttcccgatg gcgtattaaa cgtcataaat ggtactggct ctgtggtcgg gcaaacctta     660
tgtgaaagcc ccatcactaa aatgatcacc atgacaggct ccactgtcgc gggtaaacaa     720
atttataaaa ccagcgcaga gtatatgacc cctgtcatgc ttgagttagg tggtaaagcg     780
ccgatggtcg tcatggatga tgccgatctt gataaggcgg cagaagatgc actgtggggg     840
cgttttgcca actgcggaca ggtatgcact tgtgtagaac gcttatatgt tcatgcaagt     900
gtttacgatg agtttatggc taaattctta cctttagtga aagggttgaa agtcggggat     960
cccatggatg cagactcaca aatgggccct aagtgtaacc agcgtgaaat tgataatatc    1020
gaccacatag tgcatgaagc catcaagcaa ggtgcaacgg ttgccactgg cggtaagacg    1080
gcaacagttg aaggcttcga aggcggctgt tggtatgagc ccaccgtttt agtggatgtt    1140
aaacaagaca atatagtggt gcacgaagaa accttcggcc ccattctacc tatcgttaaa    1200
gtcagtagta tggaacaagc tatcgagttt tgtaacgaca gcatctatgg tttaagcgct    1260
tacgtacaca cccaaagctt tgccaatatt aatcaagcta tcagtgattt agaagtcggt    1320
gaagtgtata tcaaccgcgg aatgggtgag cagcatcagg gcttccacaa cggctggaaa    1380
caaagcggtt ttggcggtga agacggtaag tttggccttg agcaatactt ggaaaagaaa    1440
accgtttata tcaatgaggc t                                              1461
```

<210> SEQ ID NO 7
<211> LENGTH: 1458
<212> TYPE: DNA
<213> ORGANISM: Q93p88: Microscilla sp. PRE1

<400> SEQUENCE: 7

```
atgattatgt caacagtaaa aaattataaa ctttacatcg atggagagtg gatagacgct      60
accaccggtg aatcacagga aatccttagc ccaacggacg aaactgtcgt ggggacagta     120
cagatgggtg tagaggcaga tgcacaaatt gccttagaag ctgcggaaag ggcacagaaa     180
cagtggaaaa aagtacctgc aagaaaacgc gcggatttgc tccgcacttt tgcggctgaa     240
atcaaagcca ataagaatca acttgctgaa ttacttgtga gagagcaggg taagcttttg     300
gcagtagcca aaatggaagt ggaagtgaca gcgtcattca tagagtatgc gtgtgacggt     360
gccagaagca tcgaaggtga tatcattcct tcagacaacc ctgctgagca tattatgatc     420
```

-continued

```
cacaaaattc cccggggagt tgtagtggct attacagcgt ggaatttccc attggctctt    480

gcgggaagaa agcttggacc tgctttggta gccggcaact cggtggtatt aaagcctacg    540

caggaaacac cgatagctac gcttgaactt ggaaatatag ccaataaggt aggtttacct    600

aaaggcctaa tcaatattct aacaggtcag ggcagtgtgc tgggtaatgc cctggtagcc    660

aacccgatta ccaaaatggt gtctatgaca ggtagtactc ctgcaggtca gcagatcttc    720

cgtacggcag cagaaaacct tatccatgtt cagttggagc tgggtggaaa ggcaccatgt    780

attgtatttg atgatgctga tctggagcag gctgtagagg gtgcttttca ttcaagattt    840

gataactgcg gccaggtatg tacgagcaat gagcgactgt atgtccacga gagcatctac    900

aatgaattca tggagcgctt tatggagaaa gtcaaaggtt tgaaattagg aaaccccatg    960

gatgcagcga cgaccattgg tcctaaggtg aatgccaagg aagtagcgca tatggaacat   1020

ctcgtgacaa aaagcgtgga ggaaggagct accgtggcta taggaggtaa aaagcctcag   1080

ggtaaggcat ttgaaaaagg tcactggttt gagcctacta tcttaacgga tgtaaagcag   1140

aatatgacca tagttcatga ggagtctttt ggtcccattc ttccggtaat taagttcagt   1200

gagttcaatg aggtcattgg atatgccaat gattgtgaat acggtttggc tgctatggta   1260

tttactaacg acatgaataa gatcatgcga ttgaacgatg agctcgaatt tggagaaatc   1320

tatatcaata gaggccatgg cgaacaacat cagggattcc ataatggcta caaattgagt   1380

gggacaggtg gagaagatag taagtatgga tttgagcagt atatggagaa aaaaaccttc   1440

tatatcaaat acaaagcc                                                 1458
```

<210> SEQ ID NO 8
<211> LENGTH: 1458
<212> TYPE: DNA
<213> ORGANISM: D5EN35: Coraliomargarita akajimensis

<400> SEQUENCE: 8

```
ctactcgctg aagttcacat acatggtttt cttctcgaga tagttctcgt agccgtactt     60

gccgtcttcg ccgccggtac cactgagctt gtagccattg tggaagccct gacgttgttc    120

acccattggg cggttgacgt agatctcgcc gaattcgagt tccagcacgg cgcgctggat    180

gaggcgcata tccttggtga agaggaaggc ggccagaccg tagtcgctgt cgttggcgag    240

ttcgagggct tcttcgtagc tggagatctt catgatcggg ctgacgacac cgaagacttc    300

ttcgcgcata acgtccatgc tgttgtcgca accggtcaga atggtgggct cgtaccagtg    360

gcccttttca tattgggcac cttccggacg cttgccgccg caaaccaagc ttgctccttg    420

ctcaattgcc ttgtcgacga tcttaccaat ggcctcggtt tcgtaggcgt tgaccttagg    480

gccgatgttg gtggatggat cgagtggatc accaatggtc agtttcttta cctcatcggt    540

gtacttggcc aggaactcgt cgtagtgctt ctcgtggata tagaaacgtt cggggcaggt    600

gcagacctgg ccgctgttca aatggcggga aaccactgca gccgaaactg ctttatcgac    660

atcgccgtct tccagtagga tgaagggagc cttaccgccg agttcgaggc gaacagcagt    720

gagattgtct gcgctgtcct tgaaaatttg ctgacccgtt ttggtgctac cagtcatggt    780

aaccagcttg gtgagcttat tcttcaccaa ttccgagccc atggtggaac cgccgccggt    840

tacgatgttg agcacgccat ccggaatgcc agcttctttg gcaagcttgc cgagttcgag    900

tacggcgcat ggagtcaccg atggtggctt gacgaccatc gagttgcctg ccgtcaatgc    960

cgggccgatc ttgcggcaag cgagggcgag cgggaaattc caagcagcga tgccaacagt   1020

cacgccatag ggaaccttgt ggatccaaat gtgttcgttg ggcaggtcgg aggaatagat   1080
```

-continued

```
gtcgccttcc gtgcgacggg cggattgcgc tgggaagttg atgaagtctg cagagacgtc   1140

gacttcaccc agcgcaagtt cataggtctt gcccatttca atgctcagta ggcgagcgag   1200

gcgttcacgg tttgctttaa ttaagtcagc aaacttgatt agtacgttgc cgcgttcgac   1260

cgcaggaatg gctgcccatg ccggttgggc ttgcttggcg ctttgcaggg cacgttcagc   1320

atcggcagcg tcgccgtcct gtacggtagc gatgactgct tcattggatg ggttctcgac   1380

ttcaacgatc ttgccggaag tggcgtcgac ccattcgccg tgaatataca tttggtaggc   1440

ggtaattgta tcagtgct                                                  1458


<210> SEQ ID NO 9
<211> LENGTH: 49
<212> TYPE: DNA
<213> ORGANISM: Artificial Sequence
<220> FEATURE:
<223> OTHER INFORMATION: Forward primer to amplify AHGD from S.
      degradans(SdeAHGD)

<400> SEQUENCE: 9

ggcggtggtg gcggcatgaa aattcataac atgaaaaatt ttatcaacg                 49


<210> SEQ ID NO 10
<211> LENGTH: 47
<212> TYPE: DNA
<213> ORGANISM: Artificial Sequence
<220> FEATURE:
<223> OTHER INFORMATION: Reverse primer to amplify AHGD from S.
      degradans(SdeAHGD)

<400> SEQUENCE: 10

gttcttctcc tttgcgcccc tatcattcag caaaatacac tgtcttc                   47


<210> SEQ ID NO 11
<211> LENGTH: 47
<212> TYPE: DNA
<213> ORGANISM: Artificial Sequence
<220> FEATURE:
<223> OTHER INFORMATION: Forward primer to amplify AHGD from P.
      atlantica (PatlAHGD)

<400> SEQUENCE: 11

ggcggtggtg gcggcatgac tgttcaagat ttacacttta aaaacaa                   47


<210> SEQ ID NO 12
<211> LENGTH: 47
<212> TYPE: DNA
<213> ORGANISM: Artificial Sequence
<220> FEATURE:
<223> OTHER INFORMATION: Reverse primer to amplify AHGD from P.
      atlantica (PatlAHGD)

<400> SEQUENCE: 12

gttcttctcc tttgcgcccc tactaagcct cattgatata aacggtt                   47
```